(12) United States Patent
Lukocs et al.

(10) Patent No.: US 8,084,401 B2
(45) Date of Patent: Dec. 27, 2011

(54) NON-VOLATILE PHOSPHORUS HYDROCARBON GELLING AGENT

(75) Inventors: Brent Lukocs, Rimbey (CA); Shaun Mesher, Calgary (CA); Thomas P Wilson, Jr., Floresville, TX (US); Tina Garza, San Antonio, TX (US); Wayne Mueller, Airdrie (CA); Frank Zamora, San Antonio, TX (US); Larry W. Gatlin, San Antonio, TX (US)

(73) Assignee: Clearwater International, LLC, Houston, TX (US)

( * ) Notice: Subject to any disclaimer, the term of this patent is extended or adjusted under 35 U.S.C. 154(b) by 1180 days.

(21) Appl. No.: 11/339,303

(22) Filed: Jan. 25, 2006

(65) Prior Publication Data
US 2007/0173413 A1    Jul. 26, 2007

(51) Int. Cl.
*C09K 8/64* (2006.01)
*C09K 8/74* (2006.01)
*C09K 8/528* (2006.01)
*C02F 5/10* (2006.01)
*C23G 1/06* (2006.01)
*E21B 43/26* (2006.01)

(52) U.S. Cl. ........ 507/238; 507/235; 507/266; 507/269; 507/274; 166/305.1

(58) Field of Classification Search ............ 507/238, 507/235, 266, 269, 274; 166/305.1
See application file for complete search history.

(56) References Cited

U.S. PATENT DOCUMENTS

| | | | |
|---|---|---|---|
| 2,196,042 A | 4/1940 | Timpson | 23/11 |
| 2,390,153 A | 12/1945 | Kern | 260/72 |
| 3,059,909 A | 10/1962 | Wise | 261/39.3 |
| 3,163,219 A | 12/1964 | Wyant et al. | 166/283 |
| 3,301,723 A | 1/1967 | Chrisp | 149/20 |
| 3,301,848 A | 1/1967 | Halleck | 536/123.1 |
| 3,303,896 A | 2/1967 | Tillotson et al. | 175/69 |
| 3,317,430 A | 5/1967 | Priestley et al. | 510/503 |
| 3,565,176 A | 2/1971 | Wittenwyler | 166/270 |
| 3,755,503 A * | 8/1973 | Stanford | 558/158 |
| 3,856,921 A | 12/1974 | Shrier et al. | 423/228 |
| 3,888,312 A | 6/1975 | Tiner et al. | 166/308.5 |
| 3,933,205 A | 1/1976 | Kiel | 166/308.1 |
| 3,937,283 A | 2/1976 | Blauer et al. | 166/307 |
| 3,960,736 A | 6/1976 | Free et al. | 507/216 |
| 3,965,982 A | 6/1976 | Medlin | 166/249 |
| 3,990,978 A | 11/1976 | Hill | 507/235 |
| 4,007,792 A | 2/1977 | Meister | 166/308.2 |
| 4,052,159 A | 10/1977 | Fuerst et al. | |
| 4,067,389 A | 1/1978 | Savins | 166/246 |
| 4,108,782 A | 8/1978 | Thompon | 507/205 |
| 4,112,050 A | 9/1978 | Sartori et al. | 423/223 |
| 4,112,051 A | 9/1978 | Sartori et al. | 423/223 |
| 4,112,052 A | 9/1978 | Sartori et al. | 423/223 |
| 4,113,631 A | 9/1978 | Thompson | 507/202 |
| 4,378,845 A | 4/1983 | Medlin et al. | 166/297 |
| 4,461,716 A | 7/1984 | Barbarin et al. | 252/307 |
| 4,479,041 A | 10/1984 | Fenwick et al. | 200/81 R |
| 4,506,734 A | 3/1985 | Nolte | 166/308.1 |
| 4,514,309 A | 4/1985 | Wadhwa | 507/211 |
| 4,541,935 A | 9/1985 | Constien et al. | 507/225 |
| 4,549,608 A | 10/1985 | Stowe et al. | 166/280.1 |
| 4,553,596 A | 11/1985 | Graham et al. | 166/295 |
| 4,561,985 A | 12/1985 | Glass, Jr. | 507/108 |
| 4,623,021 A | 11/1986 | Stowe | 166/250.1 |
| 4,654,266 A | 3/1987 | Kachnik | 428/403 |
| 4,657,081 A | 4/1987 | Hodge | 166/380.5 |
| 4,660,643 A | 4/1987 | Perkins | 166/283 |
| 4,683,068 A | 7/1987 | Kucera | 507/201 |
| 4,686,052 A | 8/1987 | Baranet et al. | 507/244 |
| 4,695,389 A | 9/1987 | Kubala | 507/244 |
| 4,705,113 A | 11/1987 | Perkins | 166/302 |
| 4,714,115 A | 12/1987 | Uhri | 166/308.1 |
| 4,718,490 A | 1/1988 | Uhri | 166/281 |
| 4,724,905 A | 2/1988 | Uhri | 166/250.1 |
| 4,725,372 A | 2/1988 | Teot et al. | 507/129 |
| 4,739,834 A | 4/1988 | Peiffer et al. | 166/308.4 |
| 4,741,401 A | 5/1988 | Walles et al. | 166/300 |
| 4,748,011 A | 5/1988 | Baize | 423/228 |
| 4,779,680 A | 10/1988 | Sydansk | 166/300 |
| 4,795,574 A | 1/1989 | Syrinek et al. | 507/238 |
| 4,817,717 A | 4/1989 | Jennings, Jr. et al. | 166/278 |
| 4,830,106 A | 5/1989 | Uhri | 166/250.1 |
| 4,846,277 A | 7/1989 | Khalil et al. | 166/280.1 |
| 4,848,468 A | 7/1989 | Hazlett et al. | 166/300 |
| 4,852,650 A | 8/1989 | Jennings, Jr. et al. | 166/250.1 |
| 4,869,322 A | 9/1989 | Vogt, Jr. et al. | 166/280.1 |
| 4,892,147 A | 1/1990 | Jennings, Jr. et al. | 166/280.2 |
| 4,926,940 A | 5/1990 | Stromswold | 166/247 |

(Continued)

FOREIGN PATENT DOCUMENTS

CA          2125513          1/1995

(Continued)

OTHER PUBLICATIONS

U.S. Appl. No. 12/075,461, filed Mar. 11, 2008, Gatlin et al.
U.S. Appl. No. 11/554,834, filed Oct. 31, 2006, Venditto et al.
U.S. Appl. No. 11/765,306, filed Jun. 19, 2007, Kakadjian et al.
U.S. Appl. No. 11/748,248, filed May 14, 2007, Thompson et al.
U.S. Appl. No. 11/736,971, filed Apr. 18, 2007, Kippie et al.
U.S. Appl. No. 11/767,384, filed Jun. 22, 2007, Sweeney et al.
U.S. Appl. No. 11/741,110, filed Apr. 27, 2007, Wilson, Jr. et al.
U.S. Appl. No. 11/677,434, filed Feb. 21, 2007, Wanner et al.
U.S. Appl. No. 11/736,992, filed Apr. 18, 2007, Zamora et al.
U.S. Appl. No. 11/760,581, filed Jun. 8, 2007, Schwartz.
U.S. Appl. No. 12/029,335, filed Feb. 11, 2008, Kakadjian et al.
Sartori, F. and Savage, D.W., Sterically Hindered Amines for CO2 Removal from Gases, Ind. Eng. Chem. Fundam. 1983, 22, 239-249.

(Continued)

Primary Examiner — Timothy J. Kugel
Assistant Examiner — Atnaf Admasu
(74) Attorney, Agent, or Firm — Robert W Strozier

(57) ABSTRACT

New fluids are disclosed for use in servicing subterranean formations containing oil and gas. In particular, an improved chemical gelling additive for hydrocarbon based fracturing fluids is disclosed having reduce, negligible or no volatile phosphorus at temperatures below about 250° C.

29 Claims, 6 Drawing Sheets

U.S. PATENT DOCUMENTS

| | | | | |
|---|---|---|---|---|
| 4,938,286 A | 7/1990 | Jennings, Jr. | | 166/280.1 |
| 4,978,512 A | 12/1990 | Dillon | | 423/226 |
| 5,005,645 A | 4/1991 | Jennings, Jr. et al. | | 166/280.1 |
| 5,024,276 A | 6/1991 | Borchardt | | 166/308.6 |
| 5,067,556 A | 11/1991 | Fudono et al. | | 62/196.4 |
| 5,074,359 A | 12/1991 | Schmidt | | 166/280.1 |
| 5,074,991 A | 12/1991 | Weers | | 208/236 |
| 5,082,579 A | 1/1992 | Dawson | | 507/211 |
| 5,106,518 A | 4/1992 | Cooney et al. | | 507/21 |
| 5,110,486 A | 5/1992 | Manalastas et al. | | 507/260 |
| 5,169,411 A | 12/1992 | Weers | | 44/421 |
| 5,190,675 A * | 3/1993 | Gross | | 507/238 |
| 5,224,546 A | 7/1993 | Smith et al. | | 166/300 |
| 5,228,510 A | 7/1993 | Jennings, Jr. et al. | | 166/263 |
| 5,246,073 A | 9/1993 | Sandiford et al. | | 166/295 |
| 5,259,455 A | 11/1993 | Nimerick et al. | | 166/308.5 |
| 5,330,005 A | 7/1994 | Card et al. | | 166/280.2 |
| 5,342,530 A | 8/1994 | Aften et al. | | 252/8.551 |
| 5,347,004 A | 9/1994 | Rivers et al. | | 544/180 |
| 5,363,919 A | 11/1994 | Jennings, Jr. | | 166/308.1 |
| 5,402,846 A | 4/1995 | Jennings, Jr. et al. | | 166/259 |
| 5,411,091 A | 5/1995 | Jennings, Jr. | | 166/280.1 |
| 5,424,284 A | 6/1995 | Patel et al. | | 507/129 |
| 5,439,055 A | 8/1995 | Card et al. | | 166/280.2 |
| 5,462,721 A | 10/1995 | Pounds et al. | | 423/226 |
| 5,465,792 A | 11/1995 | Dawson et al. | | 166/295 |
| 5,472,049 A | 12/1995 | Chaffe et al. | | 166/250.1 |
| 5,482,116 A | 1/1996 | El-Rabaa et al. | | 166/250.1 |
| 5,488,083 A | 1/1996 | Kinsey, III et al. | | 507/211 |
| 5,497,831 A | 3/1996 | Hainey et al. | | 166/308.1 |
| 5,501,275 A | 3/1996 | Card et al. | | 166/280.2 |
| 5,551,516 A | 9/1996 | Norman et al. | | 166/308.2 |
| 5,624,886 A | 4/1997 | Dawson et al. | | 507/217 |
| 5,635,458 A | 6/1997 | Lee et al. | | 507/240 |
| 5,649,596 A | 7/1997 | Jones et al. | | 166/300 |
| 5,669,447 A | 9/1997 | Walker et al. | | 166/300 |
| 5,674,377 A | 10/1997 | Sullivan, III et al. | | 208/208 R |
| 5,688,478 A | 11/1997 | Pounds et al. | | 423/228 |
| 5,693,837 A | 12/1997 | Smith et al. | | 556/148 |
| 5,711,396 A | 1/1998 | Joerg et al. | | 180/444 |
| 5,722,490 A | 3/1998 | Ebinger | | 166/281 |
| 5,744,024 A | 4/1998 | Sullivan, III et al. | | 208/236 |
| 5,755,286 A | 5/1998 | Ebinger | | 166/281 |
| 5,775,425 A | 7/1998 | Weaver et al. | | 166/276 |
| 5,787,986 A | 8/1998 | Weaver et al. | | 166/280.2 |
| 5,806,597 A | 9/1998 | Tjon-Joe-Pin et al. | | 166/300 |
| 5,807,812 A | 9/1998 | Smith et al. | | 507/238 |
| 5,833,000 A | 11/1998 | Weaver et al. | | 166/276 |
| 5,853,048 A | 12/1998 | Weaver et al. | | 166/276 |
| 5,871,049 A | 2/1999 | Weaver et al. | | 166/276 |
| 5,877,127 A | 3/1999 | Card et al. | | 507/273 |
| 5,908,073 A | 6/1999 | Nguyen et al. | | 166/276 |
| 5,908,814 A | 6/1999 | Patel et al. | | 507/131 |
| 5,964,295 A | 10/1999 | Brown et al. | | 166/308.2 |
| 5,979,557 A | 11/1999 | Card et al. | | 166/300 |
| 5,980,845 A | 11/1999 | Cherry | | 423/229 |
| 6,016,871 A | 1/2000 | Burts, Jr. | | 166/300 |
| 6,035,936 A | 3/2000 | Whalen | | 166/308.5 |
| 6,047,772 A | 4/2000 | Weaver et al. | | 166/276 |
| 6,054,417 A | 4/2000 | Graham et al. | | 507/238 |
| 6,059,034 A | 5/2000 | Rickards et al. | | 166/280.2 |
| 6,060,436 A | 5/2000 | Snyder et al. | | 507/266 |
| 6,069,118 A | 5/2000 | Hinkel et al. | | 507/277 |
| 6,123,394 A | 9/2000 | Jeffrey | | 299/16 |
| 6,133,205 A | 10/2000 | Jones | | 507/276 |
| 6,147,034 A | 11/2000 | Jones et al. | | 507/238 |
| 6,162,449 A | 12/2000 | Maier et al. | | 424/401 |
| 6,162,766 A | 12/2000 | Muir et al. | | 507/277 |
| 6,169,058 B1 | 1/2001 | Le et al. | | 507/222 |
| 6,228,812 B1 | 5/2001 | Dawson et al. | | 507/221 |
| 6,247,543 B1 | 6/2001 | Patel et al. | | 175/64 |
| 6,267,938 B1 | 7/2001 | Warrender et al. | | 423/226 |
| 6,283,212 B1 | 9/2001 | Hinkel et al. | | 166/279 |
| 6,291,405 B1 | 9/2001 | Lee et al. | | 507/136 |
| 6,330,916 B1 | 12/2001 | Rickards et al. | | 166/280.2 |
| 6,482,777 B2 * | 11/2002 | Cain | | 508/185 |
| 6,725,931 B2 | 4/2004 | Nguyen et al. | | 166/280.2 |
| 6,756,345 B2 | 6/2004 | Pakulski et al. | | 507/246 |
| 6,793,018 B2 | 9/2004 | Dawson et al. | | 166/300 |
| 6,832,650 B2 | 12/2004 | Nguyen et al. | | 166/279 |
| 6,875,728 B2 | 4/2005 | Gupta et al. | | 507/240 |
| 7,140,433 B2 | 11/2006 | Gatlin et al. | | 166/250.01 |
| 7,268,100 B2 | 9/2007 | Kippie et al. | | 507/244 |
| 7,316,275 B2 | 1/2008 | Wang et al. | | 166/300 |
| 7,350,579 B2 | 4/2008 | Gatlin et al. | | 166/308.3 |
| 7,622,054 B2 * | 11/2009 | Delgado et al. | | 252/182.35 |
| 2002/0049256 A1 | 4/2002 | Bergeron, Jr. | | 514/674 |
| 2002/0165308 A1 | 11/2002 | Kinniard et al. | | 524/492 |
| 2003/0220204 A1 | 11/2003 | Baran, Jr. et al. | | 507/200 |
| 2005/0045330 A1 | 3/2005 | Nguyen et al. | | 166/281 |
| 2005/0092489 A1 | 5/2005 | Welton et al. | | 166/280.2 |
| 2005/0130847 A1 | 6/2005 | Gatlin et al. | | |
| 2005/0137114 A1 | 6/2005 | Gatlin et al. | | 510/424 |
| 2005/0153846 A1 | 7/2005 | Gatlin | | 208/236 |
| 2005/0250666 A1 | 11/2005 | Gatlin et al. | | 510/492 |
| 2006/0116296 A1 | 6/2006 | Kippie et al. | | |
| 2006/0194700 A1 | 8/2006 | Gatlin et al. | | 507/203 |
| 2007/0032693 A1 | 2/2007 | Gatlin et al. | | 507/239 |
| 2007/0129257 A1 | 6/2007 | Kippie et al. | | 507/102 |
| 2007/0131425 A1 | 6/2007 | Gatlin et al. | | 166/280.2 |
| 2007/0173413 A1 | 7/2007 | Lukocs et al. | | 507/238 |
| 2007/0173414 A1 | 7/2007 | Wilson, Jr. | | 507/131 |
| 2008/0039345 A1 | 2/2008 | Kippie et al. | | 507/213 |

FOREIGN PATENT DOCUMENTS

| | | |
|---|---|---|
| CA | 2007965 | 2/1996 |
| CN | 1101369 | 4/1995 |
| CN | 1101369 A | 4/1995 |
| DE | 4027300 | 5/1992 |
| EP | 0730018 A1 | 9/1996 |
| GB | 775376 | 10/1954 |
| GB | 816337 A | 7/1959 |
| GB | 1073338 A | 6/1967 |
| GB | 1177134 | 1/1970 |
| GB | 1177134 A | 1/1970 |
| GB | 1355080 A | 5/1971 |
| GB | 1355080 | 6/1974 |
| GB | 2348897 A1 | 3/2000 |
| GB | 2348897 | 10/2000 |
| GB | 2424664 | 10/2006 |
| JP | 10001461 | 6/1988 |
| JP | 08151422 | 11/1996 |
| JP | 10110115 A | 4/1998 |
| JP | 2005194148 A | 7/2005 |
| WO | WO 98/19774 | 5/1998 |
| WO | WO 98/56497 | 12/1998 |
| WO | WO 00/31220 | 6/2000 |
| WO | WO 00/31220 A1 | 6/2000 |

OTHER PUBLICATIONS

Fushslueger, U., Socher, G., Grether, H-J., Grasserbauer, M., Capillary Supercritical Fluid Chromatography/Mass Spectroscopy of Phenolic Mannich Bases with Dimethyl Ether Modified Ethane as Mobile Phase, Anal. Chem., 1999, 71, 2324-2333.

Kauffman, W.J., Observations on the Synthesis and Characterization of N,N',N"-Tris-(dimethylaminopropyly)hexahydro-s-triazine and isolable intermediates, XP009005168.

Delepine, M., Effect of Hydrogen Sulfide on Trimethyltrimethyl Triamine, Bull. Soc. Chim., 1896, 14, 889-891 (English Translation).

Delepine, M., Effect of Hydrogen Sulfide and Trimethyltrimethyl Triamine, Ann. Chim. Phys., 1896, 4, 114-133 (English Translation).

Paquin, A.M., Reaction of Primary Amines with Aliphatic Aldehydes, Chem. Ber., 1949, 82, 316-326 (English Translation).

Castillo, M., Avila, Y.S., Rodrigues, R.E., Viloria, A., H2S Liquid Scavengers, Their Corrosivity Properites and the Compatibility with Other Down Stream Processes, Corrosion 2000, paper 00491.

GB Search Report, Jul. 31, 2008, UK Pat. Office.

Journal of Materials Research, 1999, vol. 14(2), pp. 327-329.

U.S. Appl. No. 11/328,432, filed Jan. 9, 2006, Wilson.

U.S. Appl. No. 11/293,859, filed Dec. 2, 2005, Kippie et al.

U.S. Appl. No. 11/298,547, filed Dec. 9, 2005, Gatlin et al.

U.S. Appl. No. 11/298,556, filed Dec. 9, 2005, Gatlin et al.

U.S. Appl. No. 11/545,387, filed Oct. 10, 2006, Gatlin et al.

\* cited by examiner

US 8,084,401 B2

NON-VOLATILE PHOSPHORUS HYDROCARBON GELLING AGENT

BACKGROUND OF THE INVENTION

1. Field of the Invention

The present invention relates to methods for reducing the deposition of volatile phosphorus compounds in fractionation towers, distillation columns, or other high temperature hydrocarbon separation equipment.

More particularly, the present invention relates to methods for reducing the deposition of volatile phosphorus compounds in fractionation towers, distillation columns, or other high temperature hydrocarbon separation equipment, where the method includes the step supplying to a producing well a production fluid including a phosphorus compound having reduced volatility.

2. Description of the Related Art

Prior art fluid that include phosphorus-containing compounds have been implicated causing fouling in the fraction towers and other separation units in oil and gas processing stations and in oil and gas refineries. Volatile phosphorus-containing compounds can be determined by using a test method for the determination of Organo-Phosphorus in Volatile Distillates of Crude Oil by Inductively Coupled Plasma. The method is approved by Canadian refineries and was established by Maxim Analytics, Inc. of Edmonton, Alberta, Canada.

The problem with volatile phosphorus-containing compounds is that they cause fouling in the separation units such as fractionation tower in refineries. This problem can be traced to phosphate esters present in fluid used to fracture formation and to increase oil and/or gas production. Volatile phosphorus-containing compounds tend to condense in the towers at 250° C. and below. The problem has been addressed in such U.S. patents as U.S. Pat. Nos. 6,849,581 & 6,875,728. These patents all deal with different chemistries designed to reduce the problem.

However, there is still a need in the art for improved fracturing and production fluids that include a phosphorus-containing compounds which produces reduced or no volatile phosphorus compounds, which during any of a number of separation process including fractionation reduce or eliminate the deposition of volatile phosphorus.

SUMMARY OF THE INVENTION

The present invention provides a fracturing and/or production fluid including a phosphorus-containing compound having reduced volatility at distillation and/or separation temperatures.

The present invention also provides a method for producing a formation including the step of supplying to the formation a fluid including a phosphorus-containing compound having reduced volatility to produce a production fluid, and forwarding the production fluid to a high temperature separation unit where the phosphorus-containing compound reduces or eliminates fouling due to volatile phosphorus-containing compounds.

The present invention provides a method for fracturing a formation including the step of injecting a fracturing fluid into a formation, where the fluid includes a base fluid and a cross-linkable composition includes a gelling agent and a cross-linking agent, where the base fluid is a hydrocarbon.

The present invention also provides a method for completing a well including the steps of circulating a completion fluid in the well, where the fluid includes a base fluid and a cross-linkable composition includes a gelling agent and a cross-linking agent, where the base fluid is a hydrocarbon.

The present invention also provides a method for production of a well including the steps of injecting a production fluid into a well to aid in oil and/or gas production, where the fluid includes a base fluid and a cross-linkable composition includes a gelling agent and a cross-linking agent, where the base fluid is a hydrocarbon.

The present invention also provides a method for making non volatility phosphate ester comprising the step of contacting phosphorus pentoxide with an alkoxide donor under conditions of temperature, pressure and time sufficient to produce a phosphate ester product, where the alkoxide moieties having at least four carbon atoms, one or more of which can be nitrogen or oxygen. The alkoxide donor is selected from the group consisting of mono-alkyl-phosphates, di-alkyl-phosphates, tri-alkyl-phosphates, alcohols or mixtures or combinations thereof, where the alkyl groups and the alcohol all have at least 4 carbon atoms, one or more of which can be nitrogen or oxygen.

The present invention also provides a method for making non volatility oil field fluid comprising the step of adding a phosphorus ester product of this invention to a oil field fluid as a gelling agent, where the fluid have reduced phosphate volatility at temperatures up to about 250° C.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
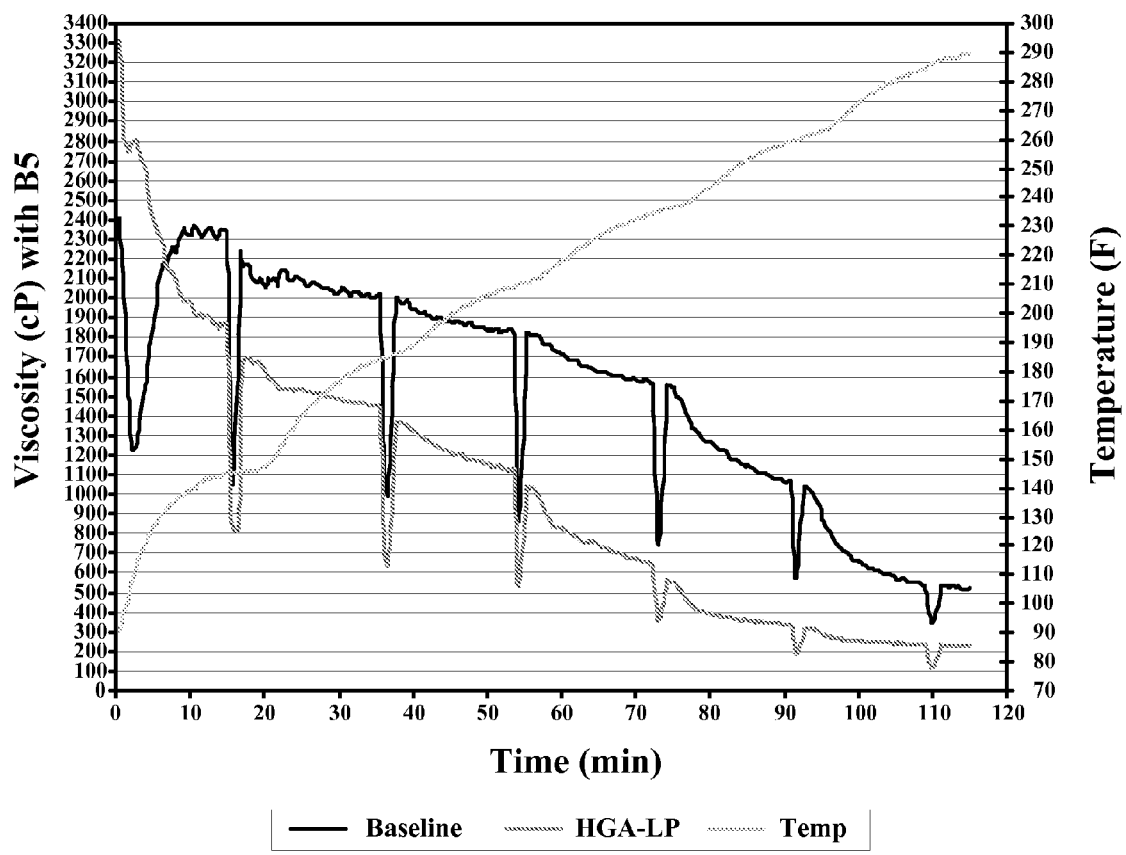
FIG. 1 is a plot depicting the viscosity verses temperature behavior of a fluid embodiment of this invention.

The inventors have found a process for the removal of volatile phosphorus-containing compounds used to viscosify hydrocarbon fracturing fluids, viscosified hydrocarbon fluids including non-volatile phosphorus-containing compounds and broken hydrocarbon fluids including non-volatile phosphorus-containing compounds from. The inventors have found that methods and compositions can be developed for gelling and breaking hydrocarbon fluids that do not generate volatile phosphorus-containing compounds. The phosphorus-containing compounds can be used in gelling and breaking hydrocarbon fluids that do not generate volatile phosphorus-containing compounds at temperatures below 250° C., as measured using a laboratory analytical method approved by the Canadian Crude Quality Technical Association for determining volatile phosphorus-containing compounds and referred to herein as the CCQTA test. The inventors have found that suitable viscosified completion, production and fracturing fluids can be prepared including phosphorus-containing compounds having reduced volatility at temperature below about 250° C. The inventor believe that refinery operations will see a significant decrease in phosphorus content in any deposits found in fractionation towers operated at temperatures between about 200° C. and about 250° C.

Chemical additives are used widely within the petroleum industry. Applications include, without limitation, refining, drilling, completion, and transportation such as pipelines. Chemical additives are used extensively in the completion applications to viscosify water and/or oil based completion and/or fracturing fluids. A hydraulic fracturing treatment is one common application employing chemical additives to viscosity (commonly referred to as a gelled fluid) a hydrocarbon fluid, in which a subterranean formation is stimulated. In addition to including the viscosity additives, the completion or fracturing fluid can contain silica, ceramic or natural materials (proppants) used to prop open the fractures created using the fracturing fluid. After the placement of the proppants in the subterranean formation, additional chemicals contained in the fluid start to break down the viscosifying agents in the fluid; these additives are called breakers. The breakers reduce the viscosity of the fluids to facilitate recovery of fluids from the formation. The returned broken fracturing and/or completion fluids contain a significant portion of the deactivated gelling agent, produced water, formation and proppant fines. This broken fluid will enter crude oil pipelines and be shipped to a refinery for processing, typically in very low concentrations.

Recently, problems have arisen within the refining industry processing crude oil streams containing broken gelled hydrocarbon fluids. Fractionation tower fouling has been observed at several refineries that gave rise to a consortium group to investigate potential sources for the unexpected and premature tower fouling. A group was formed called the Canadian Crude Quality Technical Association (CCQTA). This group has debated the issue for several years. The group determined that phosphorus was a significant component of the foulant and traced the phosphorus back to additive usage during production or upstream processing. Since its inception, the project has dealt with various phases of contaminant and key additive identification, elucidation of the fouling mechanism, the development of both chemical and process alternatives, and the proposal of crude oil specifications. CCQTA identified certain phosphate esters used in hydraulic fracturing as containing volatile phosphorus. Volatile phosphorus compounds are believed to be present in crude oil streams that make it through de-salters and into distillation towers. At a temperature around 250° C., volatile phosphorus condenses in the towers and brings a number of other inorganic and organic deposits out with it. Such deposits have been analyzed to contain about 8-12% phosphorus and are blamed for the short run time of towers in the group. A procedure for determining the amount of volatile phosphorus in crude oil or broken gelled hydrocarbon fluids has been created with the aid of the CCQTA and is referred to herein as the CCQTA test.

The present invention broadly relates to upstream oil processing fluids having reduced volatile phosphorus values, the fluids includes abase fluid and a cross-linkable composition includes a gelling agent and a cross-linking agent, where the base fluid is a hydrocarbon. The gelling agent comprises a phosphate ester formed from an alkoxide donor, where the alkyl group of the alkoxide donor has at least 4 carbon atoms and generally between 4 and 20 carbon atoms, one or more of which can be hetero atoms selected from the group of oxygen and nitrogen. In certain embodiments, the alkoxide donor is a tri-alkyl-phosphate such as tributyl-phosphate, which has a higher boiling point than triethyl phosphate, the commonly used phosphate for preparing phosphate ester for use in oil field fluids. Oil field fluid including phosphate ester made using tributyl phosphate showed no volatile phosphorus at temperatures up to 250° C.

The present invention also broadly relates to method for fracturing and producing oil and/or gas wells, including the steps of injecting a fluid including a base fluid and a cross-linkable composition includes a gelling agent and a cross-linking agent, where the base fluid is a hydrocarbon fluid and the fluid has reduced volatility in the presence or absence of a proppant and forwarding the produced fluids, after de-salting, to a high temperature distillation or other separation unit, where the de-salted, produced fluids produce less to no volatile phosphorus compounds at temperatures up to 250° C. The gelling agent comprises a phosphate esters formed from tri-alkyl-phosphates, where the alkyl group has between 4 and 20 carbon atoms, one or more of which can be hetero atoms selected from the group of oxygen and nitrogen. In certain embodiments, the tri-alkyl-phosphate is tributyl-phosphate, which has a higher boiling point than triethyl phosphate, the commonly used phosphate for preparing phosphate ester for use in oil field fluids. Oil field fluid including phosphate ester made using tributyl phosphate showed no volatile phosphorus at temperatures up to 250° C.

The present invention broadly relates to method for producing less volatile phosphate ester including the step of contacting phosphorus pentoxide with a trialkyl phosphate in the presence of an alcohol, where the alkyl groups are the same or different and have at least four carbon atoms, generally from about 4 to about 16 carbon atoms or mixtures or combinations thereof, where one or more of the carbon atoms can be replaced with a hetero atom selected from the group consisting of oxygen and nitrogen to form a phosphate ester product having an acid value @ pH 5 to 5.5 of between about 190 and about 210 and an acid value @ pH 9 to 9.5 of between about 230 and about 260. The phosphate ester product is believed to be a mixture of $PO(OR)_3$, $PO(OR)_2(OH)$ and $PO(OR)(OH)_2$, with little or no $PO(OR)_3$, where the R group is derived from either the trialkyl phosphate or from the alcohol, but regardless, the number of carbon atoms is at least 4.

In certain embodiments, the tri-alkyl phosphate includes from about 4 to about 20 carbon atoms, one or more of the carbon atoms can be replaced with a hetero atom selected from the group consisting of oxygen and nitrogen. In certain embodiments, the tri-alkyl phosphate includes from about 4 to about 12 carbon atoms, one or more of the carbon atoms can be replaced with a hetero atom selected from the group consisting of oxygen and nitrogen. In certain embodiments, the tri-alkyl phosphate includes 4 carbon atoms, one or more of the carbon atoms can be replaced with a hetero atom selected from the group consisting of oxygen and nitrogen. In certain embodiment, the alcohol has from about 4 to 20 carbon atoms or mixtures or combinations thereof, where one or more of the carbon atoms can be replaced with a hetero atom selected from the group consisting of oxygen and nitrogen. However, alkyl phosphate and/or lower alcohols can be used as well provided amount of alkyl groups having at least 4 carbon atoms, the temperature, the pressure and the time are sufficient to evaporate all alkyl group as their alcohol having least than 4 carbon atoms, one or more of which can be nitrogen or oxygen. In certain embodiment, the alcohol has from about 4 to 16 carbon atoms or mixtures or combinations thereof, where one or more of the carbon atoms can be replaced with a hetero atom selected from the group consisting of oxygen and nitrogen. In certain other embodiments, the method is carried out in the presence of an alcohol having from about 6 to about 12 carbon atoms, or mixtures or combinations thereof and where one or more of the carbon atoms can be replaced with a hetero atom selected from the group consisting of oxygen and nitrogen. In certain other embodiments, the method is carried out in the presence of an alcohol having from about 8 to about 10 carbon atoms, or mixtures or combinations thereof and where one or more of the carbon atoms can be replaced with a hetero atom selected from the group consisting of oxygen and nitrogen. The alkyl groups in both the tri-alkyl phosphate and the alcohol can be linear, branched, saturated, unsaturated, cyclic, acyclic or mixtures or combinations thereof. In certain embodiments, the alkyl groups are saturated linear alkyl groups. In certain embodiments, an acid value @ pH 5 to 5.5 is between about 195 and about 205 and acid value @ pH 9 to 9.5 of between about 235 and about 255.

The present invention also relates to method for producing less volatile phosphate ester including the step of contacting phosphorus pentoxide with a trialkyl phosphate with mixing at a first elevated temperature, pressure and for a first period of time sufficient, where the temperature is generally between about 200° F. and about 300° F., the pressure is atmospheric or near atmospheric (where the term near means that the pressure can be 100 psi above or below atmospheric) and the first period of time is generally between about 0.5 hours and 8 hours, with longer times allowed. After the first step, an alcohols or mixture of alcohols is added and mixing is continued at a second elevated temperature and for a second period of time, where the second elevated temperature is generally between about 200° F. and about 300° F. and the second period of time is generally between about 0.5 minutes and 8 hours to form a phosphate ester product as set forth above. The embodiments described above for the one step process are equally applicable to this two step process.

In certain embodiments, the second temperature is higher than the first temperature and the second period of time is longer than the first period of time. In certain embodiments, the first temperature is between about 230° F. and about 260° F. and the first period of time is between about 0.5 hour and about 3 hours, while the second temperature is between about 240° F. and about 270° F. and the second period of time is between about 2 hours and about 6 hours. In certain embodiments, the first temperature is between about 235° F. and about 255° F. and the first period of time is between about 1 hours to about 3 hours, while the second temperature is between about 245° F. and about 265° F. and the second period of time is between about 3 hours and about 5 hours. In certain embodiments, the first temperature is between about 240° F. and about 250° F. and the first period of time is between about 2 hours, while the second temperature is between about 250° F. and about 260° F. and the second period of time is between about 4 hours.

The present invention also relates to method for producing less volatile phosphate ester including the step of contacting phosphorus pentoxide with an alcohol with mixing at an elevated temperature and for a period of time sufficient, where the temperature is generally between about 200° F. and about 300° F. and the period of time is generally between about 0.5 hours and 8 hours, with longer times allowed. The alcohol useful in this process are alcohols having at least three carbon atoms, one or more carbon atoms can be replace by O or N, or mixtures or combinations of such alcohols. In certain embodiments, the alcohols have between 4 and 20 carbon atoms, one or more carbon atoms can be replace by O or N, or mixtures or combinations of such alcohols. In certain embodiments, the alcohols have between 4 and 16 carbon atoms, one or more carbon atoms can be replace by O or N, or mixtures or combinations of such alcohols. In certain embodiments, the alcohols have between 4 and 12 carbon atoms, one or more carbon atoms can be replace by O or N, or mixtures or combinations of such alcohols. In certain embodiments, the alcohols have between 4 and 10 carbon atoms, one or more carbon atoms can be replace by O or N, or mixtures or combinations of such alcohols. In certain embodiments, the alcohols have between 6 and 16 carbon atoms, one or more carbon atoms can be replace by O or N, or mixtures or combinations of such alcohols. In certain embodiments, the alcohols have between 6 and 12 carbon atoms, one or more carbon atoms can be replace by O or N, or mixtures or combinations of such alcohols. In certain embodiments, the alcohols have between 6 and 10 carbon atoms, one or more carbon atoms can be replace by O or N, or mixtures or combinations of such alcohols. In certain embodiments, the alcohols have between 8 and 16 carbon atoms, one or more carbon atoms can be replace by O or N, or mixtures or combinations of such alcohols. In certain embodiments, the alcohols have between 8 and 12 carbon atoms, one or more carbon atoms can be replace by O or N, or mixtures or combinations of such alcohols. In certain embodiments, the alcohols have between 8 and 10 carbon atoms, one or more carbon atoms can be replace by O or N, or mixtures or combinations of such alcohols. The phosphate ester product is believed to be a mixture of $PO(OR)_3$, $PO(OR)_2(OH)$ and $PO(OR)(OH)_2$, with little or no $PO(OR)_3$, where the R group is derived from either the trialkyl phosphate or from the alcohol, but regardless, the number of carbon atoms is at least 4.

Fracturing Fluids

Generally, a hydraulic fracturing treatment involves pumping a proppant-free viscous fluid, or pad, usually water with some fluid additives to generate high viscosity, into a well faster than the fluid can escape into the formation so that the pressure rises and the rock breaks, creating artificial fracture and/or enlarging existing fracture. After fracturing the formation, a propping agent such as sand is added to the fluid to form a slurry that is pumped into the newly formed fractures in the formation to prevent them from closing when the pumping pressure is released. The proppant transport ability of a base fluid depends on the type of viscosifying additives added to the water base.

Water-base fracturing fluids with water-soluble polymers added to make a viscosified solution are widely used in the art of fracturing. Since the late 1950s, more than half of the fracturing treatments are conducted with fluids comprising guar gums, high-molecular weight polysaccharides composed of mannose and galactose sugars, or guar derivatives such as hydropropyl guar (HPG), hydroxypropylcellulose (BPC), carboxymethyl guar (CMG), carboxymethylhydropropyl guar (CMHPG). Crosslinking agents based on boron, titanium, zirconium or aluminum complexes are typically used to increase the effective molecular weight of the polymer and make them better suited for use in high-temperature wells.

To a lesser extent, cellulose derivatives such as hydroxyethylcellulose (HEC) or hydroxypropylcellulose (HPC) and carboxymethylhydroxyethylcellulose (CMHEC) are also used, with or without crosslinkers. Xanthan and scleroglucan, two biopolymers, have been shown to have excellent proppant-suspension ability even though they are more expensive than guar derivatives and therefore used less frequently. Polyacrylamide and polyacrylate polymers and copolymers are used typically for high-temperature applications or friction reducers at low concentrations for all temperatures ranges.

Polymer-free, water-base fracturing fluids can be obtained using viscoelastic surfactants. These fluids are normally prepared by mixing in appropriate amounts of suitable surfactants such as anionic, cationic, nonionic and zwitterionic surfactants. The viscosity of viscoelastic surfactant fluids is attributed to the three dimensional structure formed by the components in the fluids. When the concentration of surfactants in a viscoelastic fluid significantly exceeds a critical concentration, and in most cases in the presence of an electrolyte, surfactant molecules aggregate into species such as micelles, which can interact to form a network exhibiting viscous and elastic behavior.

Cationic viscoelastic surfactants—typically consisting of long-chain quaternary ammonium salts such as cetyltrimethylammonium bromide (CTAB)—have been so far of primarily commercial interest in wellbore fluid. Common reagents that generate viscoelasticity in the surfactant solutions are salts such as ammonium chloride, potassium chloride, sodium chloride, sodium salicylate and sodium isocyanate and non-ionic organic molecules such as chloroform. The electrolyte content of surfactant solutions is also an important control on their viscoelastic behavior. Reference is made for example to U.S. Pat. Nos. 4,695,389, 4,725,372, 5,551,516, 5,964,295, and 5,979,557, incorporated herein by reference. However, fluids comprising this type of cationic viscoelastic surfactants usually tend to lose viscosity at high brine concentration (10 pounds per gallon or more). Therefore, these fluids have seen limited use as gravel-packing fluids or drilling fluids, or in other applications requiring heavy fluids to balance well pressure. Anionic viscoelastic surfactants are also used.

It is also known from International Patent Publication WO 98/56497, to impart viscoelastic properties using amphoteric/zwitterionic surfactants and an organic acid, salt and/or inorganic salt. The surfactants are for instance dihydroxyl alkyl glycinate, alkyl ampho acetate or propionate, alkyl betaine, alkyl amidopropyl betaine and alkylamino mono- or di-propionates derived from certain waxes, fats and oils. The surfactants are used in conjunction with an inorganic water-soluble salt or organic additives such as phthalic acid, salicylic acid or their salts. Amphoteric/zwitterionic surfactants, in particular those comprising a betaine moiety are useful at temperature up to about 150° C. and are therefore of particular interest for medium to high temperature wells. However, like the cationic viscoelastic surfactants mentioned above, they are usually not compatible with high brine concentration.

According to a preferred embodiment of the invention, the treatment consists in alternating viscoelastic-base fluid stages (or a fluid having relatively poor proppant capacity, such as a polyacrylamide-based fluid, in particular at low concentration) with stages having high polymer concentrations. Preferably, the pumping rate is kept constant for the different stages but the proppant-transport ability may be also improved (or alternatively degraded) by reducing (or alternatively increasing) the pumping rate.

The proppant type can be sand, intermediate strength ceramic proppants (available from Carbo Ceramics, Norton Proppants, etc.), sintered bauxites and other materials known to the industry. Any of these base propping agents can further be coated with a resin (available from Santrol, a Division of Fairmount Industries, Borden Chemical, etc.) to potentially improve the clustering ability of the proppant. In addition, the proppant can be coated with resin or a proppant flowback control agent such as fibers for instance can be simultaneously pumped. By selecting proppants having a contrast in one of such properties such as density, size and concentrations, different settling rates will be achieved.

"Waterfrac" treatments employ the use of low cost, low viscosity fluids in order to stimulate very low permeability reservoirs. The results have been reported to be successful (measured productivity and economics) and rely on the mechanisms of asperity creation (rock spalling), shear displacement of rock and localized high concentration of proppant to create adequate conductivity. It is the last of the three mechanisms that is mostly responsible for the conductivity obtained in "waterfrac" treatments. The mechanism can be described as analogous to a wedge splitting wood.

Viscous well treatment fluids are commonly used in the drilling, completion, and treatment of subterranean formations penetrated by wellbores. A viscous well treatment fluid is generally composed of a polysaccharide or synthetic polymer in an aqueous solution which is crosslinked by an organometallic compound. Examples of well treatments in which metal-crosslinked polymers are used are hydraulic fracturing, gravel packing operations, water blocking, and other well completion operations.

Hydraulic fracturing techniques are widely employed to enhance oil and gas production from subterranean formations. During hydraulic fracturing, fluid is injected into a well bore under high pressure. Once the natural reservoir pressures are exceeded, the fracturing fluid initiates a fracture in the formation which generally continues to grow during pumping. As the fracture widens to a suitable width during the course of the treatment, a propping agent is then also added to the fluid. The treatment design generally requires the fluid to reach a maximum viscosity as it enters the fracture which affects the fracture length and width. The viscosity of most fracturing fluids is generated from water-soluble polysaccharides, such as galactomannans or cellulose derivatives. Employing crosslinking agents, such as borate, titanate, or zirconium ions, can further increase the viscosity. The gelled fluid may be accompanied by a propping agent (i.e., proppant) which results in placement of the proppant within the fracture thus produced. The proppant remains in the produced fracture to prevent the complete closure of the fracture and to form a conductive channel extending from the well bore into the formation being treated once the fracturing fluid is recovered.

In order for the treatment to be successful, it is preferred that the fluid viscosity eventually diminish to levels approaching that of water after the proppant is placed. This allows a portion of the treating fluid to be recovered without producing excessive amounts of proppant after the well is opened and returned to production. The recovery of the fracturing fluid is accomplished by reducing the viscosity of the fluid to a lower value such that it flows naturally from the formation under the influence of formation fluids. This viscosity reduction or conversion is referred to as "breaking" and can be accomplished by incorporating chemical agents, referred to as "breakers," into the initial gel.

Certain gels of fracturing fluids, such as those based upon guar polymers, undergo a natural break without the intervention of a breaking agent. However, the breaking time for such gelled fluids generally is excessive and impractical, being somewhere in the range from greater than 24 hours to in excess of weeks, months, or years depending on reservoir conditions. Accordingly, to decrease the break time of gels used in fracturing, chemical agents are usually incorporated into the gel and become a part of the gel itself. Typically, these agents are either oxidants or enzymes which operate to degrade the polymeric gel structure. Most degradation or "breaking" is caused by oxidizing agents, such as persulfate salts (used either as is or encapsulated), chromous salts, organic peroxides or alkaline earth or zinc peroxide salts, or by enzymes.

In addition to the importance of providing a breaking mechanism for the gelled fluid to facilitate recovery of the fluid and to resume production, the timing of the break is also of great importance. Gels which break prematurely can cause suspended proppant material to settle out of the gel before being introduced a sufficient distance into the produced fracture. Premature breaking can also lead to a premature reduction in the fluid viscosity, resulting in a less than desirable fracture width in the formation causing excessive injection pressures and premature termination of the treatment.

On the other hand, gelled fluids which break too slowly can cause slow recovery of the fracturing fluid from the produced fracture with attendant delay in resuming the production of formation fluids and severely impair anticipated hydrocarbon production. Additional problems may occur, such as the tendency of proppant to become dislodged from the fracture, resulting in at least partial closing and decreased efficiency of the fracturing operation. Preferably, the fracturing gel should begin to break when the pumping operations are concluded. For practical purposes, the gel preferably should be completely broken within about 24 hours after completion of the fracturing treatment. Gels useful in this regard include those disclosed in U.S. Pat. Nos. 3,960,736; 5,224,546; 6,756,345; and 6,793,018, incorporated herein by reference.

Fracturing fluid compositions of this invention comprise a solvent, a polymer soluble or hydratable in the solvent, a crosslinking agent, an inorganic breaking agent, an optional ester compound and a choline carboxylate. Preferably, the solvent includes water, and the polymer is hydratable in water. The solvent may be an aqueous potassium chloride solution. The inorganic breaking agent may be a metal-based oxidizing agent, such as an alkaline earth metal or a transition metal. The inorganic breaking agent may be magnesium peroxide, calcium peroxide, or zinc peroxide. The ester compound may be an ester of a polycarboxylic acid. For example, the ester compound may be an ester of oxalate, citrate, or ethylene diamine tetraacetate. The ester compound having hydroxyl groups can also be acetylated. An example of this is that citric acid can be acetylated to form acetyl triethyl citrate. A presently preferred ester is acetyl triethyl citrate. The hydratable polymer may be a water soluble polysaccharide, such as galactomannan, cellulose, or derivatives thereof. The crosslinking agent may be a borate, titanate, or zirconium-containing compound. For example, the crosslinking agent can be sodium borate×$H_2O$ (varying waters of hydration), boric acid, borate crosslinkers (a mixture of a titanate constituent, preferably an organotitanate constituent, with a boron constituent. The organotitanate constituent can be TYZOR® titanium chelate esters from E.I du Pont de Nemours & Company. The organotitanate constituent can be a mixture of a first organotitanate compound having a lactate base and a second organotitanate compound having triethanolamine base. The boron constituent can be selected from the group consisting of boric acid, sodium tetraborate, and mixtures thereof. These are described in U.S. Pat. No. 4,514,309, incorporated herein by reference, borate based ores such as ulexite and colemanite, Ti(IV) acetylacetonate, Ti(IV) triethanolamine, Zr lactate, Zr triethanolamine, Zr lactate-triethanolamine, or Zr lactate-triethanolamine-triisopropanolamine. In some embodiments, the well treatment fluid composition may further comprise a proppant.

In another aspect, the invention relates to a well treatment fluid composition. The composition includes a solvent, a polymer soluble or hydratable in the solvent, a crosslinking agent, an alkaline earth metal or a transition metal-based breaking agent, an optional ester of a carboxylic acid and choline carboxylate. The breaking agent may be magnesium peroxide, calcium peroxide, or zinc peroxide. The solvent may include water, and the polymer is hydratable in water. The solvent may be an aqueous potassium chloride solution. The hydratable polymer may be a polysaccharide.

In still another aspect, the invention relates to a method of treating a subterranean formation. The method comprises: formulating a fracturing fluid comprising a solvent, a polymer soluble or hydratable in the solvent, a crosslinking agent, an inorganic breaking agent, a choline carboxylate and an optional ester compound; and injecting the fracturing fluid into a bore hole to contact at least a part of the formation by the fracturing fluid under a sufficient pressure to fracture the formation. The fracturing fluid has a viscosity that changes in response to a condition. The method may further comprise removing the fracturing fluid after the viscosity of the fracturing fluid is reduced. In some embodiments, the method may further comprise injecting a proppant into the formation. The proppant may be injected into the formation with the fracturing fluid. The fracturing fluid may have a pH at or above about 7. Preferably, the fracturing fluid should have a pH in the range of about 8 to about 12. The inorganic breaking agent may be a metal-based oxidizing agent. The metal may be an alkaline earth metal or a transition metal. The inorganic breaking agent may be magnesium peroxide, calcium peroxide, or zinc peroxide. The optional ester compound may be an ester of an polycarboxylic acid, such as an ester of oxalate, citrate, or ethylene diamine tetraacetate. Preferably, the solvent includes water, and the polymer is a water soluble polysaccharide, such as galactomannan, cellulose, or derivatives thereof. The solvent may be an aqueous potassium chloride solution. The crosslinking agent may be a borate, titanate, or zirconium-containing compound. The fracturing fluid can further comprise sodium thiosulfate.

Embodiments of the invention provide a well treatment fluid composition and a method of using the fluid composition to treat subterranean formations. The well treatment fluid composition can be used in hydraulic fracturing as a fracturing fluid, gravel packing operations, water blocking, temporary plugs for purposes of wellbore isolation and/or fluid loss control and other well completion operations. Most well treatment fluids are aqueous, although non-aqueous fluids may be formulated and used as well.

The well treatment fluid composition comprises a solvent (such as water), a polymer soluble or hydratable in the solvent, a crosslinking agent, an inorganic breaking agent, a choline carboxylate of and an optional ester compound. Optionally, the well treatment fluid composition may further include various other fluid additives, such as pH buffers, biocides, stabilizers, propping agents (i.e., proppants), mutual solvents, and surfactants designed to prevent emulsion with formation fluids, to reduce surface tension, to enhance load recovery, and/or to foam the fracturing fluid. The well treatment fluid composition may also contain one or more salts, such as potassium chloride, magnesium chloride, sodium chloride, calcium chloride, tetramethyl ammonium chloride, and mixtures thereof. It is found that a fracturing fluid made in accordance with embodiments of the invention exhibits reduced or minimal premature breaking and breaks completely or substantially completely after a well treatment is finished.

"Premature breaking" as used herein refers to a phenomenon in which a gel viscosity becomes diminished to an undesirable extent before all of the fluid is introduced into the formation to be fractured. Thus, to be satisfactory, the gel viscosity should preferably remain in the range from about 50% to about 75% of the initial viscosity of the gel for at least two hours of exposure to the expected operating temperature. Preferably the fluid should have a viscosity in excess of 100 centipoise (cP) at 100 sec$^{-1}$ while injection into the reservoir as measured on a Fann 50 C viscometer in the laboratory.

"Complete breaking" as used herein refers to a phenomenon in which the viscosity of a gel is reduced to such a level that the gel can be flushed from the formation by the flowing formation fluids or that it can be recovered by a swabbing operation. In laboratory settings, a completely broken, non-crosslinked gel is one whose viscosity is about 10 cP or less as measured on a Model 35 Fann viscometer having a RIBI rotor and bob assembly rotating at 300 rpm.

An aqueous fracturing fluid may be prepared by blending a hydratable polymer with an aqueous base fluid. The base aqueous fluid can be, for example, water or brine. Any suitable mixing apparatus may be used for this procedure. In the case of batch mixing, the hydratable polymer and aqueous fluid are blended for a period of time which is sufficient to form a hydrated sol.

Suitable hydratable polymers that may be used in embodiments of the invention include any of the hydratable polysaccharides which are capable of forming a gel in the presence of a crosslinking agent. For instance, suitable hydratable polysaccharides include, but are not limited to, galactomannan gums, glucomannan gums, guars, derived guars, and cellulose derivatives. Specific examples are guar gum, guar gum derivatives, locust bean gum, Karaya gum, carboxymethyl cellulose, carboxymethyl hydroxyethyl cellulose, and hydroxyethyl cellulose. Presently preferred gelling agents include, but are not limited to, guar gums, hydroxypropyl guar, carboxymethyl hydroxypropyl guar, carboxymethyl guar, and carboxymethyl hydroxyethyl cellulose. Suitable hydratable polymers may also include synthetic polymers, such as polyvinyl alcohol, polyacrylamides, poly-2-amino-2-methyl propane sulfonic acid, and various other synthetic polymers and copolymers. Other suitable polymers are known to those skilled in the art.

The hydratable polymer may be present in the fluid in concentrations ranging from about 0.10% to about 5.0% by weight of the aqueous fluid. A preferred range for the hydratable polymer is about 0.20% to about 0.80% by weight.

A suitable crosslinking agent can be any compound that increases the viscosity of the fluid by chemical crosslinking, physical crosslinking, or any other mechanisms. For example, the gellation of a hydratable polymer can be achieved by crosslinking the polymer with metal ions including boron, zirconium, and titanium containing compounds, or mixtures thereof. One class of suitable crosslinking agents is organotitanates. Another class of suitable crosslinking agents is borates as described, for example, in U.S. Pat. No. 4,514,309, incorporated herein by reference. The selection of an appropriate crosslinking agent depends upon the type of treatment to be performed and the hydratable polymer to be used. The amount of the crosslinking agent used also depends upon the well conditions and the type of treatment to be effected, but is generally in the range of from about 10 ppm to about 1000 ppm of metal ion of the crosslinking agent in the hydratable polymer fluid. In some applications, the aqueous polymer solution is crosslinked immediately upon addition of the crosslinking agent to form a highly viscous gel. In other applications, the reaction of the crosslinking agent can be retarded so that viscous gel formation does not occur until the desired time.

The pH of an aqueous fluid which contains a hydratable polymer can be adjusted if necessary to render the fluid compatible with a crosslinking agent. Preferably, a pH adjusting material is added to the aqueous fluid after the addition of the polymer to the aqueous fluid. Typical materials for adjusting the pH are commonly used acids, acid buffers, and mixtures of acids and bases. For example, sodium bicarbonate, potassium carbonate, sodium hydroxide, potassium hydroxide, and sodium carbonate are typical pH adjusting agents. Acceptable pH values for the fluid may range from neutral to basic, i.e., from about 5 to about 14. Preferably, the pH is kept neutral or basic, i.e., from about 7 to about 14, more preferably between about 8 to about 12.

The term "breaking agent" or "breaker" refers to any chemical that is capable of reducing the viscosity of a gelled fluid. As described above, after a fracturing fluid is formed and pumped into a subterranean formation, it is generally desirable to convert the highly viscous gel to a lower Viscosity fluid. This allows the fluid to be easily and effectively removed from the formation and to allow desired material, such as oil or gas, to flow into the well bore. This reduction in viscosity of the treating fluid is commonly referred to as "breaking". Consequently, the chemicals used to break the viscosity of the fluid is referred to as a breaking agent or a breaker.

There are various methods available for breaking a fracturing fluid or a treating fluid. Typically, fluids break after the passage of time and/or prolonged exposure to high temperatures. However, it is desirable to be able to predict and control the breaking within relatively narrow limits. Mild oxidizing agents are useful as breakers when a fluid is used in a relatively high temperature formation, although formation temperatures of 300° F. (149° C.) or higher will generally break the fluid relatively quickly without the aid of an oxidizing agent.

Examples of inorganic breaking agents for use in this invention include, but are not limited to, persulfates, percarbonates, perborates, peroxides, perphosphates, permanganates, etc. Specific examples of inorganic breaking agents include, but are not limited to, alkaline earth metal persulfates, alkaline earth metal percarbonates, alkaline earth metal perborates, alkaline earth metal peroxides, alkaline earth metal perphosphates, zinc salts of peroxide, perphosphate, perborate, and percarbonate, and so on. Additional suitable breaking agents are disclosed in U.S. Pat. Nos. 5,877,127; 5,649,596; 5,669,447; 5,624,886; 5,106,518; 6,162,766; and 5,807,812, incorporated herein by reference. In some embodiments, an inorganic breaking agent is selected from alkaline earth metal or transition metal-based oxidizing agents, such as magnesium peroxides, zinc peroxides, and calcium peroxides.

In addition, enzymatic breakers may also be used in place of or in addition to a non-enzymatic breaker. Examples of suitable enzymatic breakers such as guar specific enzymes, alpha and beta amylases, amyloglucosidase, aligoglucosidase, invertase, maltase, cellulase, and hemi-cellulase are disclosed in U.S. Pat. Nos. 5,806,597 and 5,067,566, incorporated herein by reference.

A breaking agent or breaker may be used "as is" or be encapsulated and activated by a variety of mechanisms including crushing by formation closure or dissolution by formation fluids. Such techniques are disclosed, for example, in U.S. Pat. Nos. 4,506,734; 4,741,401; 5,110,486; and 3,163,219, incorporated herein by reference.

Suitable ester compounds include any ester which is capable of assisting the breaker in degrading the viscous fluid in a controlled manner, i.e., providing delayed breaking initially and substantially complete breaking after well treatment is completed. An ester compound is defined as a compound that includes one or more carboxylate groups: R—COO—, wherein R is phenyl, methoxyphenyl, alkylphenyl, $C_1$-$C_{11}$ alkyl, $C_1$-$C_{11}$ substituted alkyl, substituted phenyl, or other organic radicals. Suitable esters include, but are not limited to, diesters, triesters, etc.

An ester is typically formed by a condensation reaction between an alcohol and an acid by eliminating one or more water molecules. Preferably, the acid is an organic acid, such as a carboxylic acid. A carboxylic acid refers to any of a family of organic acids characterized as polycarboxylic acids and by the presence of more than one carboxyl group. In additional to carbon, hydrogen, and oxygen, a carboxylic acid may include heteroatoms, such as S, N, P, B, Si, F, Cl, Br, and I. In some embodiments, a suitable ester compound is an ester of oxalic, malonic, succinic, malic, tartaric, citrate, phthalic, ethylenediaminetetraacetic (EDTA), nitrilotriacetic, phosphoric acids, etc. Moreover, suitable esters also include the esters of glycolic acid. The alkyl group in an ester that comes from the corresponding alcohol includes any alkyl group, both substituted or unsubstituted. Preferably, the alkyl group has one to about ten carbon atoms per group. It was found that the number of carbon atoms on the alkyl group affects the water solubility of the resulting ester. For example, esters made from $C_1$-$C_2$ alcohols, such as methanol and ethanol, have relatively higher water solubility. Thus, application temperature range for these esters may range from about 120° F. to about 250° F. (about 49° C. to about 121° C.). For higher temperature applications, esters formed from $C_3$-$C_{10}$ alcohols, such as n-propanol, butanol, hexanol, and cyclohexanol, may be used. Of course, esters formed from $C_{11}$ or higher alcohols may also be used. In some embodiments, mixed esters, such as acetyl methyl dibutyl citrate, may be used for high temperature applications. Mixed esters refer to those esters made from polycarboxylic acid with two or more different alcohols in a single condensation reaction. For example, acetyl methyl dibutyl citrate may be prepared by condensing citric acid with both methanol and butanol and then followed by acylation.

Specific examples of the alkyl groups originating from an alcohol include, but are not limited to, methyl, ethyl, propyl, butyl, iso-butyl, 2-butyl, t-butyl, benzyl, p-methoxybenzyl, m-methoxybenxyl, chlorobenzyl, p-chlorobenzyl, phenyl, hexyl, pentyl, etc. Specific examples of suitable ester compounds include, but are not limited to, triethyl phosphate, diethyl oxalate, dimethyl phthalate, dibutyl phthalate, diethyl maleate, diethyl tartrate, 2-ethoxyethyl acetate, ethyl acetylacetate, triethyl citrate, acetyl triethyl citrate, tetracyclohexyl EDTA, tetra-1-octyl EDTA, tetra-n-butyl EDTA, tetrabenzyl EDTA, tetramethyl EDTA, etc. Additional suitable ester compounds are described, for example, in the following U.S. Pat. Nos. 3,990,978; 3,960,736; 5,067,556; 5,224,546; 4,795,574; 5,693,837; 6,054,417; 6,069,118; 6,060,436; 6,035,936; 6,147,034; and 6,133,205, incorporated herein by reference.

When an ester of a polycarboxylic acid is used, total esterification of the acid functionality is preferred, although a partially esterified compound may also be used in place of or in addition to a totally esterified compound. In these embodiments, phosphate esters are not used alone. A phosphate ester refers to a condensation product between an alcohol and a phosphorus acid or a phosphoric acid and metal salts thereof. However, in these embodiments, combination of a polycarboxylic acid ester with a phosphate ester may be used to assist the degradation of a viscous gel.

When esters of polycarboxylic acids, such as esters of oxalic, malonic, succinic, malic, tartaric, citrate, phthalic, ethylenediaminetetraacetic (EDTA), nitrilotriacetic, and other carboxylic acids are used, it was observed that these esters assist metal based oxidizing agents (such as alkaline earth metal or zinc peroxide) in the degradation of fracturing fluids. It was found that the addition of 0.1 gal/Mgal (0.1 l/m$^3$) to 5 gal/Mgal (5 l/m$^3$) of these esters significantly improves the degradation of the fracturing fluid. More importantly, the degradation response is delayed, allowing the fracturing fluid ample time to create the fracture and place the proppant prior to the degradation reactions. The delayed reduction in viscosity is likely due to the relatively slow hydrolysis of the ester, which forms polycarboxylate anions as hydrolysis products. These polycarboxylate anions, in turn, improve the solubility of metal based oxidizing agents by sequestering the metal associated with the oxidizing agents. This may have promoted a relatively rapid decomposition of the oxidizing agent and caused the fracturing fluid degradation.

Generally, the temperature and the pH of a fracturing fluid affects the rate of hydrolysis of an ester. For downhole operations, the bottom hole static temperature ("BHST") cannot be easily controlled or changed. The pH of a fracturing fluid usually is adjusted to a level to assure proper fluid performance during the fracturing treatment. Therefore, the rate of hydrolysis of an ester could not be easily changed by altering BHST or the pH of a fracturing fluid. However, the rate of hydrolysis may be controlled by the amount of an ester used in a fracturing fluid. For higher temperature applications, the hydrolysis of an ester may be retarded or delayed by dissolving the ester in a hydrocarbon solvent. Moreover, the delay time may be adjusted by selecting esters that provide more or less water solubility. For example, for low temperature applications, polycarboxylic esters made from low molecular weight alcohols, such as methanol or ethanol, are recommended. The application temperature range for these esters could range from about 120° F. to about 250° F. (about 49° C. to about 121° C.). On the other hand, for higher temperature applications or longer injection times, esters made from higher molecular weight alcohols should preferably be used. The higher molecular weight alcohols include, but are not limited to, $C_3$-$C_6$ alcohols, e.g., n-propanol, hexanol, and cyclohexanol.

In some embodiments, esters of citric acid are used in formulating a well treatment fluid. A preferred ester of citric acid is acetyl triethyl citrate, which is available under the trade name Citraflex A2 from Morflex, Inc., Greensboro, N.C.

Propping agents or proppants are typically added to the fracturing fluid prior to the addition of a crosslinking agent. However, proppants may be introduced in any manner which achieves the desired result. Any proppant may be used in embodiments of the invention. Examples of suitable proppants include, but are not limited to, quartz sand grains, glass and ceramic beads, walnut shell fragments, aluminum pellets, nylon pellets, and the like. Proppants are typically used in concentrations between about 1 to 8 lbs. per gallon of a fracturing fluid, although higher or lower concentrations may also be used as desired. The fracturing fluid may also contain other additives, such as surfactants, corrosion inhibitors, mutual solvents, stabilizers, paraffin inhibitors, tracers to monitor fluid flow back, and so on.

The well treatment fluid composition in accordance with embodiments of the invention has many useful applications. For example, it may be used in hydraulic fracturing, gravel packing operations, water blocking, temporary plugs for purposes of wellbore isolation and/or fluid loss control, and other well completion operations. One application of the fluid composition is to use it as a fracturing fluid. Accordingly, embodiments of the invention also provide a method of treating a subterranean formation. The method includes formulating a fracturing fluid comprising an aqueous fluid, a hydratable polymer, a crosslinking agent, an inorganic breaking agent, and an ester compound; and injecting the fracturing fluid into a bore hole to contact at least a part of the formation by the fracturing fluid under a sufficient pressure to fracture the formation. Initially, the viscosity of the fracturing fluid should be maintained above at least 200 cP at 40 sec$^{-1}$ during injection and, afterwards, should be reduced to less than 200 cP at 40 sec$^{-1}$. After the viscosity of the fracturing fluid is lowered to an acceptable level, at least a portion of the fracturing fluid is removed from the formation. During the fracturing process, a proppant can be injected into the formation simultaneously with the fracturing fluid. Preferably, the fracturing fluid has a pH around or above about 7, more preferably in the range of about 8 to about 12.

It should be understood that the above-described method is only one way to carry out embodiments of the invention. The following U.S. patents disclose various techniques for conducting hydraulic fracturing which may be employed in embodiments of the invention with or without modifications: U.S. Pat. Nos. 6,169,058; 6,135,205; 6,123,394; 6,016,871; 5,755,286; 5,722,490; 5,711,396; 5,551,516; 5,497,831; 5,488,083; 5,482,116; 5,472,049; 5,411,091; 5,402,846; 5,392,195; 5,363,919; 5,228,510; 5,074,359; 5,024,276; 5,005,645; 4,938,286; 4,926,940; 4,892,147; 4,869,322; 4,852,650; 4,848,468; 4,846,277; 4,830,106; 4,817,717; 4,779,680; 4,479,041; 4,739,834; 4,724,905; 4,718,490; 4,714,115; 4,705,113; 4,660,643; 4,657,081; 4,623,021; 4,549,608; 4,541,935; 4,378,845; 4,067,389; 4,007,792; 3,965,982; and 3,933,205, incorporated herein by reference.

The liquid carrier can generally be any liquid carrier suitable for use in oil and gas producing wells. A presently preferred liquid carrier is water. The liquid carrier can comprise water, can consist essentially of water, or can consist of water. Water will typically be a major component by weight of the fluid. The water can be potable or non-potable water. The water can be brackish or contain other materials typical of sources of water found in or near oil fields. For example, it is possible to use fresh water, brine, or even water to which any salt, such as an alkali metal or alkali earth metal salt (NaCO$_3$, NaCl, KCl, etc.) has been added. The liquid carrier is preferably present in an amount of at least about 80% by weight. Specific examples of the amount of liquid carrier include 80%, 85%, 90%, and 95% by weight. The carrier liquid can be a VAS gel.

The pH of the fluid can generally be any pH compatible with downhole formations. The pH is presently preferred to be about 6.5 to about 10.0. The pH can be about the same as the formation pH.

The surfactant can generally be any surfactant. The surfactant is preferably viscoelastic. The surfactant is preferably anionic. The anionic surfactant can be an alkyl sarcosinate. The alkyl sarcosinate can generally have any number of carbon atoms. Presently preferred alkyl sarcosinates have about 12 to about 24 carbon atoms. The alkyl sarcosinate can have about 14 to about 18 carbon atoms. Specific examples of the number of carbon atoms include 12, 14, 16, 18, 20, 22, and 24 carbon atoms.

The anionic surfactant can have the chemical formula $R_1CON(R_2)CH_2X$, wherein $R_1$ is a hydrophobic chain having about 12 to about 24 carbon atoms, $R_2$ is hydrogen, methyl, ethyl, propyl, or butyl, and X is carboxyl or sulfonyl. The hydrophobic chain can be an alkyl group, an alkenyl group, an alkylarylalkyl group, or an alkoxyalkyl group. Specific examples of the hydrophobic chain include a tetradecyl group, a hexadecyl group, an octadecentyl group, an octadecyl group, and a docosenoic group.

The surfactant can generally be present in any weight percent concentration. Presently preferred concentrations of surfactant are about 0.1% to about 15% by weight. A presently more preferred concentration is about 0.5% to about 6% by weight. Laboratory procedures can be employed to determine the optimum concentrations for any particular situation.

The amphoteric polymer can generally be any amphoteric polymer. The amphoteric polymer can be a nonionic water-soluble homopolysaccharide or an anionic water-soluble polysaccharide. The polymer can generally have any molecular weight, and is presently preferred to have a molecular weight of at least about 500,000.

The polymer can be a hydrolyzed polyacrylamide polymer. The polymer can be a scleroglucan, a modified scleroglucan, or a scleroglucan modified by contact with glyoxal or glutaraldehyde. The scleroglucans are nonionic water-soluble homopolysaccharides, or water-soluble anionic polysaccharides, having molecular weights in excess of about 500,000, the molecules of which consist of a main straight chain formed of D-glucose units which are bonded by β-1,3-bonds and one in three of which is bonded to a side D-glucose unit by means of a β-1,6 bond. These polysaccharides can be obtained by any of the known methods in the art, such as fermentation of a medium based on sugar and inorganic salts under the action of a microorganism of Sclerotium type A. A more complete description of such scleroglucans and their preparations may be found, for example, in U.S. Pat. Nos. 3,301,848 and 4,561,985, incorporated herein by reference. In aqueous solutions, the scleroglucan chains are combined in a triple helix, which explains the rigidity of the biopolymer, and consequently its features of high viscosity-increasing power and resistance to shearing stress.

It is possible to use, as source of scleroglucan, the scleroglucan which is isolated from a fermentation medium, the product being in the form of a powder or of a more or less concentrated solution in an aqueous and/or aqueous-alcoholic solvent. Scleroglucans customarily used in applications in the petroleum field are also preferred according to the present invention, such as those which are white powders obtained by alcoholic precipitation of a fermentation broth in order to remove residues of the producing organism (mycelium, for example). Additionally, it is possible to use the liquid reaction mixture resulting from the fermentation and containing the scleroglucan in solution. According to the present invention, further suitable scleroglucans are the modified scleroglucan which result from the treatment of scleroglucans with a dialdehyde reagent (glyoxal, glutaraldehyde, and the like), as well as those described in U.S. Pat. No. 6,162,449, incorporated herein by reference, (β-1,3-scleroglucans with a cross-linked 3-dimensional structure produced by Sclerotium rolfsii).

The polymer can be Aquatrol V (a synthetic compound which reduces water production problems in well production; described in U.S. Pat. No. 5,465,792, incorporated hereinbyreference), AquaCon (a moderate molecular weight hydrophilic terpolymer based on polyacrylamide capable of binding to formation surfaces to enhance hydrocarbon production; described in U.S. Pat. No. 6,228,812, incorporated herein by reference) and Aquatrol C (an amphoteric polymeric material). Aquatrol V, Aquatrol C, and AquaCon are commercially available from BJ Services Company.

The polymer can be a terpolymer synthesized from an anionic monomer, a cationic monomer, and a neutral monomer. The monomers used preferably have similar reactivities so that the resultant amphoteric polymeric material has a random distribution of monomers. The anionic monomer can generally be any anionic monomer. Presently preferred anionic monomers include acrylic acid, methacrylic acid, 2-acrylamide-2-methylpropane sulfonic acid, and maleic anhydride. The cationic monomer can generally be any cationic monomer. Presently preferred cationic monomers include dimethyl-diallyl ammonium chloride, dimethylamino-ethyl methacrylate, and allyltrimethyl ammonium chloride. The neutral monomer can generally be any neutral monomer. Presently preferred neutral monomers include butadiene, N-vinyl-2-pyrrolidone, methyl vinyl ether, methyl acrylate, maleic anhydride, styrene, vinyl acetate, acrylamide, methyl methacrylate, and acrylonitrile. The polymer can be a terpolymer synthesized from acrylic acid (AA), dimethyl diallyl ammonium chloride (DMDAC) or diallyl dimethyl ammonium chloride (DADMAC), and acrylamide (AM). The ratio of monomers in the terpolymer can generally be any ratio. A presently preferred ratio is about 1:1:1.

Another presently preferred amphoteric polymeric material (hereinafter "polymer 1") includes approximately 30% polymerized AA, 40% polymerized AM, and 10% polymerized DMDAC or DADMAC with approximately 20% free residual DMDAC or DADMAC which is not polymerized due to lower relative reactivity of the DMDAC or DADMAC monomer.

The fluid can further comprise one or more additives. The fluid can further comprise a base. The fluid can further comprise a salt. The fluid can further comprise a buffer. The fluid can further comprise a relative permeability modifier. The fluid can further comprise methylethylamine, monoethanolamine, triethylamine, triethanolamine, sodium hydroxide, potassium hydroxide, potassium carbonate, sodium chloride, potassium chloride, potassium fluoride, $KH_2PO_4$, or $K_2HPO_4$. The fluid can further comprise a proppant. Conventional proppants will be familiar to those skilled in the art and include sand, resin coated sand sintered bauxite and similar materials. The proppant can be suspended in the fluid.

Relative permeability modifiers can be added to the fluids to further improve water shut off properties. These compounds are polymers that are water-soluble and improve the leak-off viscosity of the fracturing fluid.

A specific example of a treating fluid is as follows: (a) 11% KCl by weight; (b) 2.5% surfactant by weight; (c) 1.6% buffer (potassium carbonate in water (45% by weight potassium carbonate)) by volume, and (d) 1.0% of 10% (by weight) Polymer 1 solution.

An additional embodiment of the invention involves the use of any of the above described fluids in a method of fracturing a subterranean formation. The method can comprise providing a fluid comprising a liquid carrier, a viscoelastic anionic surfactant, and an amphoteric polymer, pumping the fluid through a wellbore, and contacting the fluid and the subterranean formation to fracture the formation.

A further additional embodiment of the invention involves the use of any of the above described fluids in a method of reducing the amount of water produced from a subterranean oil producing formation. The method can comprise providing a fluid comprising a liquid carrier, a viscoelastic anionic surfactant, and an amphoteric polymer, pumping the fluid through a wellbore, contacting the fluid and the subterranean formation, and obtaining product from the formation. The weight percent of water in the product is less than the weight percent of water in product produced from a similar formation that was not contacted with the fluid. The fluid can further comprise a relative permeability modifier. The $C_w$ of the similar formation that was not treated with the fluid ("untreated $C_w$") is preferably greater than the $C_w$ of the formation treated with the fluid ("treated $C_w$"). The ratio of the untreated $C_w$ to the treated $C_w$ is preferably at least about 2, at least about 5, at least about 10, at least about 20, at least about 30, at least about 40, at least about 50, at least about 60, at least about 70, at least about 80, at least about 90, at least about 100, at least about 150, or at least about 200.

According to other embodiments of the invention, there is provided a fracturing fluid comprising anionic viscoelastic surfactants which viscosify and its leak-off viscosity can be enhanced while the fluid is injected in the pores of the rock, providing water shut off and favoring oil/gas flow and allowing non damaging polymers such as relative permeability modifiers to be included in the formulations without adversely affecting the gel viscosity but improving the gel filtration efficiency and its water control properties.

Some embodiments of the invention take advantage of the natural pH change at the formation rock to cause an increase in the gel viscosity at the formation pores to block water production, which is discussed herein. For example, in its use the fluid is designed for optimum viscosity at the same pH of the formation water/rock. However it is pumped at a pH that is lower or higher than the formation pH (0.3 to 1 unit) through a wellbore and into a surrounding formation having an aqueous zone and a hydrocarbon zone. The fluid is then allowed to contact the aqueous zone and the hydrocarbon zone. Contact with the hydrocarbon zone serves to thin the fluid since the surfactant gel is thinned by hydrocarbons. While contact with the water zone or water saturated pores will lower the gel pH to that of the formation increasing its viscoelasticity and viscosity. Additionally, if an RPM polymer is included in the formulation it will adhere to the water wet rock and induce a drag, or friction force on water, reinforcing the viscoelastic gel structure and also lubricating oil production, serving to preferentially block the flow of water from that portion of the formation. Consequently oil production is unaffected while water flow is preferentially shut off.

The amphoteric polymeric material is characterized by the presence of both positively and negatively charged components along the polymer chain. This nature of the polymeric material is believed to account for the polymeric material's ability to strongly bond to the formation while exhibiting a hydrophilic character capable of forming a strong hydrogen bond to water causing a drag or a higher friction pressure on water flowing through the capillaries or openings of the formation. By whatever mechanism, the mobility of formation water is greatly reduced by the amphoteric polymeric material without restricting the production of oil or gas to any appreciable extent.

Additional description of various embodiments of the invention are provided below. The description with respect to "well-treating solution", and "viscous fluid" is applicable, with or without modifications, to the well service fluid in accordance with embodiments of the invention. It should be noted that any number disclosed herein should be understood as to mean an approximate value, regardless of whether the word "about" or "approximate" is used in describing the number.

A presently preferred well treating solution for changing the relative permeability of a formation to water can be prepared by adding the amphoteric polymeric material to VAS carrier liquid with the amphoteric polymeric material being present at about 1.0% to about 10% by volume, depending upon the permeability.

The resulting treating solution can be injected into the formation at pumping rates and treating pressures above the fracture gradient of the formation. The volume of treating solution used is based on the desired fracture geometry, the thickness of the zone to be treated, the porosity of the formation being treated, and other factors.

The viscous fluids of the invention can be used for transporting particulate through a conduit to a subterranean location. In one form, the fluids comprise an aqueous base, a surfactant comprising an alkyl sarcosinate having from about 12 to about 24 carbon atoms and a buffer for adjusting the pH of the combined aqueous base and surfactant at or for the formation pH. The alkyl sarcosinate is preferably present at about 0.5% to about 10% by weight, based upon the weight of the total fluid. The pH of the viscous fluid is preferably adjusted with the buffer to about 6.5 to about 10.0 for most formations.

The viscous fluids of the invention can also include an additional source of anions in addition to those furnished by the surfactant. The additional source of anions can be a co-surfactant such as any ionic or anionic undiluted surfactant.

In the method of fracturing a subterranean formation of the invention, an aqueous base fluid is combined with a surfactant comprising an alkyl sarcosinate having from about 12 to about 24 carbon atoms. The combined fluid is buffered to thereby adjust the pH of the combined aqueous base and surfactant at or for the formation pH, thereby creating a viscous fluid capable of supporting proppant. The viscous fluid is pumped through a wellbore and into a surrounding formation at a pressure sufficient to fracture the formation.

The viscous fluids of the invention can also be used in a method for reducing the amount of water produced from a subterranean oil producing formation. An aqueous base fluid is combined with a surfactant comprising an alkyl sarcosinate having from about 12 to about 24 carbon atoms. The combined fluid is buffered to thereby adjust the pH of the combined aqueous base and surfactant sufficiently to produce a viscous fluid. The viscous fluid is pumped through a wellbore and into a surrounding formation having an aqueous zone and a hydrocarbon zone, the aqueous zone comprising water. The viscous fluid is then allowed to contact the aqueous zone and the hydrocarbon zone. Contact with the hydrocarbon zone serves to thin the viscous fluid while contact with the aqueous zone serves to preferentially block the flow of water from that portion of the formation.

The viscoelastic surfactant fluid is useful as a fracturing fluid with improved efficiency. Specifically, the use of this fluid in fracturing a formation will simultaneously enhance oil production while simultaneously drastically minimizing or completely stopping water production.

In a preferred form, the viscous fluids of the invention comprise water, a base, a surfactant comprising an alkyl sarcosinate having from about 12 to about 24 carbon atoms in the alkyl group, and a buffer for adjusting the pH, of the combined aqueous base and surfactant at or for the formation pH. As will be explained in detail, the fluids of the invention can be optimized for viscosity and for the formation pH in order to reduce ion exchange at the formation, thereby avoiding clay dispersion and swelling. The water used in formulating the fluids can be fresh water or light brines from any convenient source. The particularly preferred alkyl sarcosinates used as the surfactant have an alkyl group of about 14 to about 18 carbon atoms.

Sarcosine (N-methylglycine) is a naturally occurring amino acid found in starfish, sea urchins and crustaceans. It can be purchased from a variety of commercial sources, or alternately produced by a number of synthetic routes known in the art including thermal decomposition of caffeine in the presence of barium hydroxide (Arch. Pharm. 232: 601, 1894); (Bull. Chem. Soc. Japan, 39: 2535, 1966); and numerous others (T. Shirai in Synthetic Production and Utilization of Amino Acids; T. Kaneko, et al., Eds.; Wiley, New York: pp. 184-186, 1974). Sodium sarcosinate is manufactured commercially from formaldehyde, sodium cyanide and methyl amine (U.S. Pat. Nos. 2,720,540 and 3,009,954). The preferred sarcosinate are the condensation products of sodium sarcosinate and a fatty acid chloride. The fatty acid chloride is reacted with sodium sarcosinate under carefully controlled alkaline conditions (i.e., the Schotten-Bauman reaction) to produce the fatty sarcosinate sodium salt which is water soluble. Upon acidification, the fatty sarcosine acid, which is also water insoluble, is formed and may be isolated from the reaction medium. The acyl sarcosines may be neutralized with bases such as the salts of sodium, potassium, ammonia, or organic bases such as triethanolamine in order to produce aqueous solutions.

Another surfactant useful in the fluids of this invention are an anionic sarcosinate surfactant available commercially from BJ Services Company as "M-Aquatrol" (MA). The MA-1 sarcosinate is a viscous liquid surfactant with at least 94% oleoyl sarcosine. For hydraulic fracturing, a sufficient quantity of the sarcosinate is present in aqueous solution to provide sufficient viscosity to suspend proppant during placement. The surfactant is preferably present at about 0.5% to about 10% by weight, most preferably at about 0.5% to about 6% by weight, based upon the weight of the total fluid.

The surfactant can be added to an aqueous solution in which there is typically dissolved a quantity of at least one water soluble salt to effect formation stability. Typical water-soluble salts include potassium chloride, sodium chloride and the like. Formation stability is typically achieved with only small concentrations of salt. The water-soluble salts may be considered part of the "buffer" for adjusting the pH of the combined aqueous base and surfactant in the method of the present invention. The viscosity of the fluids of the invention are improved significantly by the addition of certain additional anions to the surfactant-laden solution. The pH can be adjusted, for example, by the addition of alkali metal, carbonate, phosphate or borate, or organic amines, especially alkanol amines such as mono-, di- or triethanolamine.

High temperature stability of the fluids in question is achieved if selecting specific anion, such as phosphate or fluoride ions instead of chlorides, preferably provided in the form of an inorganic phosphate or fluoride salt or a fluoride acid such as fluosilicic acid ($H_2SiF_6$). The fluoride salt concentration can be about 0.5% to about 10% by weight, and more preferably about 3% to about 7% by weight, based upon the total weight of the fluid. Typical fluoride salts include ammonium bifluoride and potassium fluoride. The pH of the surfactant-fluoride salt solution can be adjusted to about 6.5 to about 10. The pH can be adjusted with the same bases as discussed above.

Each salt will produce a peak viscosity at a different pH. The fluids of invention are optimized for viscosity and formation pH as will be discussed with respect to the laboratory analyses which follow.

In the method of fracturing a formation using the formulations of the invention, an aqueous base fluid is combined with an anionic surfactant comprising an alkyl sarcosinate having from about 12 to about 24 carbon atoms, and alternatively a viscoelastic polymer such as an RPM. Standard mixing procedures known in the art can be employed since heating of the solution or special agitation procedures are not normally required. The aqueous base has been buffered with a buffer to thereby adjust the pH of the combined aqueous base and surfactant above about 6.5, thereby creating a viscous fluid capable of supporting proppant. The proppant can be added and the viscous fluid can then be pumped through a wellbore and into a surrounding formation at a pressure sufficient to fracture the formation. Typically, the viscous fluid can be allowed to contact the formation for a period of tine sufficient to increase the viscosity in the water saturated pores, while in the oil pores it will thin immediately and therefore no breakers are required.

These effects cannot be easily achieved when cationic surfactants are used. Due to the fact that cationic surfactants are not pH dependent with regards to viscosity, their viscosity remains within a narrow, un adjustable range, thereby limiting their utility. The anionic surfactants of the present invention overcome this problem by being pH dependent with regards to viscosity, thereby allowing for their viscosity to be adjusted to the desired value by altering the pH appropriately.

The fluid of the present invention may also be used as asphaltene-dispersing agents. Asphaltenes are constituents of crude oils, usually present as colloidal dispersions stabilized by resins in the oil. While examples of asphaltene-dispersing agents are know in the art (e.g. U.S. Pat. No. 5,948,237), the sarcosinate anionic surfactant of the invention in combination with RPM type materials produces a synergistic effect in this regard. Specifically, these compounds in combination form an excellent asphaltene-dispersant, thereby aiding in the cleaning of rocks, pipes, valves, conveying devices, and the like by removing heavy oil deposits and asphaltenes themselves.

The fluids of the invention can also be used as selective water control additives. The viscous fluids can be pumped into a water rich sector of a producing interval. Once placed, the gel viscosity will prevent formation water flow through that portion of the reservoir. On the other hand, gel pumped into the oil rich sector of the formation reservoir will immediately thin on contact with the oil contained within the reservoir. Consequently, oil production will be uninhibited while water flow will be preferentially stopped or significantly reduced.

For fracturing applications, the fluids of the invention are typically pumped downhole at or slightly above the formation pH. Preferably, when the fluids of the invention are used for water control purposes, the fluids are pumped downhole at about 3/10 of a pH unit less or more than the formation material pH depending on the anion portion of the salt used as counter cation. The fluid is thus pumped in a thinned state, reducing the friction pressure of the pumping job. Upon contacting the formation material, the pH of the fluid increases, resulting in complete gellation of the fluid at the formation location rather than at the well surface.

Various amine oxides have been used as surfactants to create foams and remove "intrusion fluids from wellbores," according to U.S. Pat. No. 3,303,896, incorporated herein by reference, and they have been used as foam stabilizers, according to U.S. Pat. No. 3,317,430, incorporated herein by reference. Certain amine oxides have also been used in combination with quaternary ammonium compounds as foaming and silt suspending agents. See, for example, U.S. Pat. No. 4,108,782 and U.S. Pat. No. 4,113,631, incorporated herein by reference. The use of amine oxide surfactants for chemical flooding enhanced oil recovery was described in a topical report by David K. Olsen in NIPER-417 (August 1989) for work performed for the US Department of Energy under cooperative agreement DE-FC22-83FE60149 by the National Institute for Petroleum and Energy Research. However, to Applicants'knowledge, the amine oxides have not been used to improve the properties of fracturing fluids and to promote rapid cleanup, or to enhance well production from a well stimulated by hydraulic fracturing.

Hydraulic fracturing of subterranean formations has long been established as an effective means to stimulate the production of hydrocarbon fluids from a wellbore. In hydraulic fracturing, a well stimulation fluid (generally referred to as a fracturing fluid or a "frac fluid") is injected into and through a wellbore and against the surface of a subterranean formation penetrated by the wellbore at a pressure at least sufficient to create a fracture in the formation. Usually a "pad fluid" is injected first to create the fracture and then a fracturing fluid, often bearing granular propping agents, is injected at a pressure and rate sufficient to extend the fracture from the wellbore deeper into the formation. If a proppant is employed, the goal is generally to create a proppant filled zone (aka, the proppant pack) from the tip of the fracture back to the wellbore. In any event, the hydraulically induced fracture is more permeable than the formation and it acts as a pathway or conduit for the hydrocarbon fluids in the formation to flow to the wellbore and then to the surface where they are collected. The methods of fracturing are well known and they may be varied to meet the user's needs, but most follow this general procedure (which is greatly overly simplified).

The fluids used as fracturing fluids have also been varied, but many if not most are aqueous based fluids that have been "viscosified" or thickened by the addition of a natural or synthetic polymer (cross-linked or uncross-linked). The carrier fluid is usually water or a brine (e.g., dilute aqueous solutions of sodium chloride and/or potassium chloride). The viscosifying polymer is typically a solvatable (or hydratable) polysaccharide, such as a galactomannan gum, a glycomannan gum, or a cellulose derivative. Examples of such polymers include guar, hydroxypropyl guar, carboxymethyl guar, carboxymethylhydroxyethyl guar, hydroxyethyl cellulose, carboxymethyl-hydroxyethyl cellulose, hydroxypropyl cellulose, xanthan, polyacrylamides and other synthetic polymers. Of these, guar, hydroxypropyl guar and carboxymethylhydroxyethyl guar are typically preferred because of commercial availability and cost performance.

In many instances, if not most, the viscosifying polymer is crosslinked with a suitable crosslinking agent. The crosslinked polymer has an even higher viscosity and is even more effective at carrying proppant into the fractured formation. The borate ion has been used extensively as a crosslinking agent, typically in high pH fluids, for guar, guar derivatives and other galactomannans. See, for example, U.S. Pat. No. 3,059,909, incorporated herein by reference and numerous other patents that describe this classic aqueous gel as a fracture fluid. Other crosslinking agents include, for example, titanium crosslinkers (U.S. Pat. No. 3,888,312, incorporated herein by reference), chromium, iron, aluminum, and zirconium (U.S. Pat. No. 3,301,723, incorporated herein by reference). Of these, the titanium and zirconium crosslinking agents are typically preferred. Examples of commonly used zirconium crosslinking agents include zirconium triethanolamine complexes, zirconium acetylacetonate, zirconium lactate, zirconium carbonate, and chelants of organic alphahydroxycorboxylic acid and zirconium. Examples of commonly used titanium crosslinking agents include titanium triethanolamine complexes, titanium acetylacetonate, titanium lactate, and chelants of organic alphahydroxycorboxylic acid and titanium.

Additional information on fracturing is found in the description by Janet Gulbis and Richard M. Hodge in Chapter 7 of the text "Reservoir Stimulation" published by John Wiley & Sons, Ltd. Third Edition, 2000 (Editors, Michael J. Economides and Kenneth G. Nolte), which is incorporated herein by reference. Some fracturing fluids have also been energized by the addition of a gas (e.g., nitrogen or carbon dioxide) to create a foam. See, for example, the pioneering work by Roland E. Blauer and Clarence J. Durborow in U.S. Pat. No. 3,937,283, incorporated herein by reference ("Formation Fracturing with Stable Foam"). The rheology of the traditional water-base polymer solutions and also complex fluids, such as foams, can be and typically is modified and augmented by several additives to control their performance. Fluid loss additives are typically added to reduce the loss of fracturing fluids into the formation.

The problems associated with the loss of fracturing fluid to the formation are well known. For example, in 1978 Holditch reported: "The fluid injected during the fracturing treatment will leak off into the formation and will reduce the relative permeability to gas in the invaded region. Near the fracture, the permeability to gas will be reduced to zero." In addition, Holditch said: "In some cases, the injected fracturing fluid may reduce the formation permeability in the invaded zone." Stephen A. Holditch, SPE 7561 (Presented at the $53_{rd}$ Annual Fall Technical Conference and Exhibition of the Society of Petroleum Engineers of AIME, held in Houston, Tex., Oct. 1-3, 1978). The damage to the formation could be severe, and the practical so what of that is reduced flow of hydrocarbons, low production and poor economics on the well. While the state of the art has advanced substantially since Holditch reported on the problems associated with leak off of fracturing fluid, the problems remain the same. See, for example, Vernon G. Constien, George W. Hawkins, R. K. Prud'homme and Reinaldo Navarrete, Chapter 8 entitled "Performance of Fracturing Materials" and the other chapters on fracturing and well stimulation in "Reservoir Stimulation" published by John Wiley & Sons, Ltd, Third Edition, copyright Schlumberger 2000 (Editors, Michael J. Economides and Kenneth G. Nolte), the disclosure of which is incorporated herein by reference. These authors and others emphasize the importance of "cleanup" or "fracture cleanup" to optimize production of the hydrocarbon fluids from the well. The term "cleanup" or "fracture cleanup" refers to the process of removing the fracture fluid (without the proppant) from the fracture after the fracturing process has been completed. Techniques for promoting fracture cleanup often involved reducing the viscosity of the fracture fluid as much as practical so that it will more readily flow back toward the wellbore. So-called "breakers" have been used to reduce fluid viscosity in many instances. The breakers can be enzymes (oxidizers and oxidizer catalysts), and they may be encapsulated to delay their release. See, for example, U.S. Pat. No. 4,741,401, incorporated herein by reference. Another technique to aid in the cleanup, albeit by a contrarian approach, is found in U.S. Pat. No. 6,283,212, incorporated herein by reference.

Hydraulic fracturing is a primary tool for improving well productivity by placing or extending channels from the wellbore to the reservoir. This operation is essentially performed by hydraulically injecting a fracturing fluid into a wellbore penetrating a subterranean formation and forcing the fracturing fluid against the formation strata by pressure. The formation strata or rock is forced to crack and fracture. Proppant is placed in the fracture to prevent the fracture from closing and thus, provide improved flow of the recoverable fluid, i.e., oil, gas or water.

The proppant is thus used to hold the walls of the fracture apart to create a conductive path to the wellbore after pumping has stopped. Placing the appropriate proppant at the appropriate concentration to form a suitable proppant pack is thus critical to the success of a hydraulic fracture treatment.

Sand, resin-coated sand, and ceramic particles are the most commonly used proppants, though the literature, for instance U.S. Pat. No. 4,654,266, incorporated herein by reference, also mentions the used of walnut hull fragments coated with some bonding additives, metallic shots, or metal-coated beads—nearly spherical but having a passageways to improve their conductibility.

The proppant conductivity is affected principally by two parameters, the proppant pack width and the proppant pack permeability. To improve fracture proppant conductivity, typical approaches include high large diameter proppants. More generally, the most common approaches to improve proppant fracture performance include high strength proppants, large diameter proppants, high proppant concentrations in the proppant pack to obtain wider propped fractures, conductivity enhancing materials such as breakers, flow-back aides, fibers and other material that physically alter proppant packing, and use of non-damaging fracturing fluids such as gelled oils, viscoelastic surfactant based fluids, foamed fluids or emulsified fluids. It is also recognized that grain size, grain-size distribution, quantity of fines and impurities, roundness and sphericity and proppant density have an impact on fracture conductivity.

As mentioned above, the main function of the proppant is to keep the fracture open by overcoming the in-situ stress. Where the proppant strength is not high enough, the closure stress crushes the proppant, creating fines and reducing the conductivity. Sand is typically suitable for closure stresses of less than about 6000 psi (41 MPa), resin-coated sand may be used up to about 8000 psi (55 MPa). Intermediate-strength proppant typically consists of fused ceramic or sintered-bauxite and is used for closure stresses ranging between 5000 psi and 10000 psi (34 MPa to 69 MPa). High-strength proppant, consisting of sintered-bauxite with large amounts of corundum is used at closure stresses of up to about 14000 psi (96 MPa).

Permeability of a propped fracture increases as the square of the grain diameter. However, larger grains are often more susceptible to crush, have more placement problems and tend to be more easily invaded by fines. As the result, the average conductivity over the life of a well may be actually higher with smaller proppants.

In an effort to limit the flowback of particulate proppant materials placed into the formation, it was disclosed in U.S. Pat. No. 5,330,005, incorporated herein by reference, to add some fibrous material, mixed with the proppant material. It is believed that the fibers become concentrated into a mat or other three-dimensional framework, which holds the proppant thereby limiting its flowback. The fibers can be of glass, ceramic, carbon, natural or synthetic polymers or metal fibers. They have a length of typically about 2 to 30 mm and a diameter of between 10 and 100 micrometers. According to U.S. Pat. No. 5,908,073, incorporated herein by reference, the flowback is prevented through the use of fibrous bundles, made of from about 5 to about 200 individual fibers having lengths in the range of about 0.8 to about 2.5 mm and diameters in the range of about 10 to about 1000 micrometers. It has also known from U.S. Pat. No. 6,059,034, incorporated herein by reference, to add to blend the proppant material with a deformable particulate material. The deformable particles may have different shapes such as oval, cubic, bar-shaped, cylindrical, multi-faceted, irregular, tapered—but preferably with a maximum length-based ratio equal or less than 5, and are typically spherical plastic beads or composite particles comprising a non-deformable core and a deformable coating. In another embodiment claimed in U.S. Pat. No. 6,330,916, incorporated herein by reference, the particles may comprise ground or crushed materials such as nutshells, seed shells, fruit pits, and processed woods.

It should be emphasized that in all of the four above-mentioned U.S. patents, the proppant itself is constituted of essentially spherical particles—most typically sand—intermingled with a material that may be elongated. This reflects the general understanding of this art that angular grains fail at lower closure stresses, producing more fines and thus reducing fracture conductivity. On the other hand, round and uniform-sized grains result in higher loads before failure since stresses are more evenly distributed.

Adding fibers or fiber-like products to the products may contribute to a reduction of the proppant flowback—and consequently to a better packing of the proppant in the fracture. Additionally, they contribute to prevent fine migrations and consequently, to prevent a reduction of the proppant conductivity but there is still a need for a new type of proppant that will lead to higher conductivity.

According to the invention, the solid organic polymeric particulate matter composition is selected for its ultimate and delayed reactivity and/or degradation characteristics in providing the required gel breaking action and cleanup, it being required, of course, that its reactivity or degradation in the fluid suspension be sufficiently gradual, delayed, or retarded (delayed) that formation of a gel by the suspension is not significantly inhibited or the gelled suspension broken before the fracturing operation is carried out to the desired extent. That is, the solid organic polymeric particulate matter should not react with other components of the fluid or the particles to be removed and/or transported or the formation components, or decompose or degrade in the fluid suspension, at a rate faster than desired. The suitability of a particular solid organic polymeric particulate material or composition(s) may be determined by testing, as illustrated hereinafter, and a composition or compositions may be prepared, for example, by blending, or may be chosen, which degrade or decompose at a rate corresponding to the time required for carrying out the fracturing operation, as determined by such testing. Accordingly, the solid organic polymeric particulate matter employed in the invention may be chosen from a wide variety of organic polymeric materials of the type mentioned, provided the particles possess such delayed reactivity and/or decomposition characteristics. Thus, natural and synthetic organic polymers or elastomers having an average molecular weight of at least 10,000, preferably at least 15,000 to 18,000, and most preferably at least 100,000, as determined by size exclusion chromatography or other suitable method, having the required reactivity and/or decomposition characteristics, may be employed. As utilized herein, the expressions "organic polymeric", as applied to "compound" and to "material", and "organic polymer" and "polymer", are understood to include not only polymerization products of a monomer, but copolymers, terpolymers, etc. Additionally, all types of mixtures of the mentioned materials may be employed. For example, suitable polymeric particulate matter derived from cellulose, acrylic acid, aramides, acrylonitrile, polyamides, vinylidene, olefins, diolefins, polyester, polyurethane, vinyl alcohol, and vinyl chloride, may be used. Preferred compositions, assuming the required reactivity and/or decomposition characteristics may be selected from rayon, acetate, triacetate, cotton, wool (cellulose group); nylon, acrylic, modacrylic, nitrite, polyester, saran, spandex, vinyon, olefin, vinyl, (synthetic polymer group); azlon, rubber (protein and rubber group), and mixtures thereof. Polyester and polyamide particles of sufficient molecular weight, such as from Dacron® and nylon, respectively, and mixtures thereof, are most preferred. Again, composite particles, comprising natural and/or synthetic materials of appropriate characteristics, may be employed. For example, a suitable composite particle might comprise a core and sheath structure where the sheath material and the core material degrade over different desired periods of time. The compounds or compositions employed as organic polymeric material according to the invention need not be pure, and commercially available materials containing various additives, fillers, etc. or having coatings may be used, so long as such components do not interfere with the required activity.

As indicated, the amount of the organic polymeric particulate matter supplied will be sufficient for the task required, i.e., a sufficient or effective amount, an amount sufficient to provide a sufficient concentration of a composition or compositions which are effective to degrade the gelled suspension to the desired degree. Normally, as also indicated, this composition or compositions will comprise one or more of the ultimate reaction or decomposition products of the organic polymeric material. Preferably, the organic polymeric particulate matter level, i.e., concentration, provided initially in the fluid may range from 0.02 percent up to about 10 percent by weight of the fluid. Most preferably, however, the concentration ranges from about 0.02 percent to about 5.0 percent by weight of fluid.

Particle size and shape, while important, may be varied considerably, depending on timing and transport considerations. Preferably, if irregular or spherical particles of the organic polymer are used, particle size may range from 80 mesh to 2.5 mesh (Tyler), preferably from 60 mesh to 3 mesh. Fibers and/or platelets of the specified polymeric materials are preferred for their mobility and transfer aiding capability. In the case of fibers of the organic polymer, the fibers employed according to the invention may also have a wide range of dimensions and properties. As employed herein, the term "fibers" refers to bodies or masses, such as filaments, of natural or synthetic material(s) having one dimension significantly longer than the other two, which are at least similar in size, and further includes mixtures of such materials having multiple sizes and types. Preferably, in accordance with the invention, individual fiber lengths may range upwardly from about 1 millimeter. Practical limitations of handling, mixing, and pumping equipment in wellbore applications, currently limit the practical use length of the fibers to about 100 millimeters. Accordingly, a preferred range of fiber length will be from about 1 mm to about 100 mm or so, with a most preferred length being from at least about 2 mm up to about 30 mm. Similarly, fiber diameters will preferably range upwardly from about 5 microns, a preferred range being from about 5 microns to about 40 microns, most preferably from about 8 microns to about 20 microns, depending on the modulus of the fiber, as described more fully hereinafter. A ratio of length to diameter (assuming the cross section of the fiber to be circular) in excess of 50 is preferred. However, the fibers may have a variety of shapes ranging from simple round or oval cross-sectional areas to more complex shapes such as trilobe, figure eight, star-shape, rectangular cross-sectional, or the like. Preferably, generally straight fibers with round or oval cross sections will be used. Curved, crimped, branched, spiral-shaped, hollow, fibrillated, and other three dimensional fiber geometries may be used. Again, the fibers may be hooked on one or both ends. Fiber and platelet densities are not critical, and will preferably range from below 1 to 4 g/cm$^3$ or more.

Those skilled in the art will recognize that a dividing line between what constitute "platelets", on one hand, and "fibers", on the other, tends to be arbitrary, with platelets being distinguished practically from fibers by having two dimensions of comparable size both of which are significantly larger than the third dimension, fibers, as indicated, generally having one dimension significantly larger than the other two, which are similar in size. As used herein, the terms "platelet" or "platelets" are employed in their ordinary sense, suggesting flatness or extension in two particular dimensions, rather than in one dimension, and also is understood to include mixtures of both differing types and sizes. In general, shavings, discs, wafers, films, and strips of the polymeric material(s) may be used. Conventionally, the term "aspect ratio" is understood to be the ratio of one dimension, especially a dimension of a surface, to another dimension. As used herein, the phrase is taken to indicate the ratio of the diameter of the surface area of the largest side of a segment of material, treating or assuming such segment surface area to be circular, to the thickness of the material (on average). Accordingly, the platelets utilized in the invention will possess an average aspect ratio of from about 10 to about 10,000, preferably 100 to 1000. Preferably, the platelets will be larger than 5 microns in the shortest dimension, the dimensions of a platelet which may be used in the invention being, for example, 6 mm×2 mm×15 μm.

In a particularly advantageous aspect of the invention, particle size of the organic polymeric particulate matter may be managed or adjusted to advance or retard the reaction or degradation of the gelled suspension in the fracture. Thus, for example, of the total particulate matter content, 20 percent may comprise larger particles, e.g., greater than 100 microns, and 80 percent smaller, say 80 percent smaller than 20 micron particles. Such blending in the gelled suspension may provide, because of surface area considerations, a different time of completion of reaction or decomposition of the particulate matter, and hence the time of completion of gel decomposition or breaking, when compared with that provided by a different particle size distribution.

The selection of the fluid or liquid to form the suspension with the solid organic polymeric particulate material and other components, such as gellant and proppant, is largely a matter of choice, within the capability of those skilled in the art, and per se forms no part of the present invention. As such persons will be aware, however, the fluid, particulate material, gel forming material, etc., must be sufficiently compatible to the extent that they do not react with one another at a rate which would deleteriously interfere to any significant extent with the intended functions specified herein. Commonly, the particular fluid chosen will be determined by such considerations as treating temperature, concentration of solid material to be carried, and the desired objective. In general, any suitable fluid or liquid which provides sufficient viscosity, perhaps in conjunction with solid fibrous materials therein, to transport the proppant and other components utilized to the fracturing area or fracture, does not unduly interfere with the effectiveness of the solid particulate matter of the invention, and which results in minimal damage to the pack and to the formation, may be used, it being understood that the term "fluid", includes mixtures of such materials. The fluid will preferably be aqueous, and may comprise a gas, i.e., a foam may be employed. Any common aqueous well treatment fluid may be employed, keeping the requirements previously mentioned in mind. Suitable fluids may also include aqueous solutions of viscoelastic surfactants, i.e., surfactants which are capable of providing viscosity without requiring the addition of polymers. Fluids comprising oil-in-water emulsions may be used, and, in the appropriate instance, hydrocarbon fluids, such as diesel, may be used. Particularly preferred are the type of fracturing fluids described by Nimerick, Crown, McConnell, and Ainley in U.S. Pat. No. 5,259,455, incorporated herein by reference, and those disclosed in U.S. Pat. No. 4,686,052, incorporated herein by reference. Proportions of the components of the fluid suspension are selected to insure that fluid character, i.e., flowability, and suspension of the organic polymeric particulate material and solid material, e.g., proppant, are maintained during pumping or down well transport, i.e., an amount of the well treatment fluid or liquid is provided or present sufficient to insure fluid flow for the suspensions. Generally, the composite fluids or fluid suspensions of the invention will comprise viscous liquids.

The solid particulate matter, e.g., fibers, or fibers and/or platelet, containing fluid suspensions used in the invention may be prepared in any suitable manner or in any sequence or order. Thus, the suspension may be provided by blending in any order at the surface, and by addition, in suitable proportions, of the components to the fluid or slurry during treatment on the fly. The suspensions may also be blended offsite. In the case of some materials, which are not readily dispersible, the fibers should be "wetted" with a suitable fluid, such as water or a wellbore fluid, before or during mixing with the fracturing fluid, to allow better feeding of the fibers. Good mixing techniques should be employed to avoid "clumping" of the particulate matter.

To the extent other breaker materials are employed, the total amount of the solid particulate matter of the invention may be reduced. It is possible; however, to provide a combination of solid particulate matter in the manner of the invention along with minor amounts, i.e., less than fifty percent, of other breaker materials, such combinations providing significant transport advantages if the solid particulate matter is in the form of fibers or platelets. As will be understood by those skilled in the art, in the case where fibers and/or platelets are employed to form a porous pack upon completion of the fracturing operation or procedure, e.g., as described in the procedures of the aforementioned U.S. Pat. No. 5,439,055, incorporated herein by reference; U.S. Pat. No. 5,330,005, incorporated herein by reference; and U.S. Pat. No. 5,501,275, incorporated herein by reference, the total amount of fibers employed or pumped, assuming the use of suitable fibers as the solid organic polymeric particulate matter, will include that required for gel breaking and that for porous pack formation. As those skilled in the art will recognize, the fibers employed for pack strengthening will be chosen for durability rather than for the characteristics desired in the breaker materials selected herein, so that, in a given fracturing operation, both types of fibers may be utilized, each contributing a designed function and both contributing to or enhancing matter mobility or transport. Concentrations of "pack-forming" fibers and/or platelets in the fracturing fluid suspension for porous pack formation will be those described in the above listed patents, with even quite minor amounts of fibers and/or platelets being effective or sufficient to enhance transport.

Any suitable polymeric gel forming material or gellant, preferably water soluble, used by those skilled in the art to treat subterranean formations and form stable or stabilized gels of the fluid suspension may be employed in the invention. For simplicity hereinafter, included in the phrase "water soluble", as applied to the gellant, are those suitable polymeric materials which are dispersible or suspendable in water or aqueous liquid. Suitable gellants also include crosslinkable polymers or monomers for forming such polymers under the conditions extant. Such cross-linkable polymeric and polymer forming materials are well known, and the crosslinked polymer or polymers which produce the stable or stabilized gel are preferably formed by reacting or contacting appropriate proportions of the crosslinkable polymer with a crosslinking agent or agents. Similarly, procedures for preparing gelable compositions or fluids and conditions under which such compositions form stable gels in subterranean formations are well known to those skilled in the art. As indicated, gel-forming compositions according to the invention may be formed by mixing, in water, the water soluble crosslinkable polymer and the crosslinking agent.

In forming the gel, the crosslinkable polymer(s) and crosslinking agent and concentrations thereof are normally selected to assure (a) gel formation or presence at subterranean (i.e., formation or reservoir) conditions and (b) suitable time allotment for injection of the composition prior to the completion of gelation, or sufficient fluidity of the gelled composition to allow pumping down well. The polymer (or monomers used to form the polymer) and the crosslinking agent are generally selected and supplied in amounts effective to achieve these objectives. By "effective" amounts of the polymer or polymers (or monomers) and crosslinking agents is meant amounts sufficient to provide crosslinked polymers and form the desired stable gel under the conditions extant. Generally, a water soluble crosslinkable polymer concentration in the aqueous liquid of from about 0.05 to about 40 percent, preferably from about 0.1 percent to about 10 percent, and, most preferably, from about 0.2 percent to about 7 percent, may be employed (or sufficient monomer(s) to form these amounts of polymer). Typically, the crosslinking agent is employed in the aqueous liquid in a concentration of from about 0.001 percent to about 2 percent, preferably from about 0.005 percent to about 1.5 percent, and, most preferably, from about 0.01 percent to about 1.0 percent.

However, if a crosslinked polymer is to be used, the fluids of the invention need not contain both the crosslinkable polymer and the crosslinking agent at the surface. The crosslinkable polymer or the crosslinking agent may be omitted from the fluid sent downhole, the omitted material being introduced into the subterranean formation as a separate slug, either before, after, or simultaneously with the introduction of the fluid. In such cases, concentrations of the slugs will be adjusted to insure the required ratios of the components for proper gel formation at the desired location. Preferably, the surface formulated composition or fluid comprises at least the crosslinkable polymeric material (e.g., acrylamide, vinyl acetate, acrylic acid, vinyl alcohol, methacrylamide, ethylene oxide, or propylene oxide). More preferably, the composition comprises both (a) the crosslinking agent and (b) either (i) the crosslinkable polymer or (ii) the polymerizable monomers capable of forming a crosslinkable polymer. In treating a subterranean fracture, the formulations may be allowed to gel or begin gelation before entering the formation.

As indicated, mixtures of polymeric gel forming material or gellants may be used. Materials which may be used include water soluble crosslinkable polymers, copolymers, and terpolymers, such as polyvinyl polymers, polyacrylamides, cellulose ethers, polysaccharides, lignosulfonates, ammonium salts thereof, alkali metal salts thereof, alkaline earth salts of lignosulfonates, and mixtures thereof. Specific polymers are acrylic acid-acrylamide copolymers, acrylic acid-methacrylamide copolymers, polyacrylamides, partially hydrolyzed polyacrylamides, partially hydrolyzed polymethacrylamides, polyvinyl alcohol, polyvinyl acetate, polyalkyleneoxides, carboxycelluloses, carboxyalkylhydroxyethyl celluloses, hydroxyethylcellulose, galactomannans (e.g., guar gum), substituted galactomannans (e.g., hydroxypropyl guar), heteropolysaccharides obtained by the fermentation of starch-derived sugar (e.g., xanthan gum), ammonium and alkali metal salts thereof, and mixtures thereof. Preferred water soluble crosslinkable polymers include hydroxypropyl guar, carboxymethylhydroxypropyl guar, partially hydrolyzed polyacrylamides, xanthan gum, polyvinyl alcohol, the ammonium and alkali metal salts thereof, and mixtures thereof.

Similarly, the crosslinking agent(s) may be selected from those organic and inorganic compounds well known to those skilled in the art useful for such purpose, and the phrase "crosslinking agent", as used herein, includes mixtures of such compounds. Exemplary organic crosslinking agents include, but are not limited to, aldehydes, dialdehydes, phenols, substituted phenols, ethers, and mixtures thereof. Phenol, resorcinol, catechol, phloroglucinol, gallic acid, pyrogallol, 4,4'-diphenol, 1,3-dihydroxynaphthalene, 1,4-benzoquinone, hydroquinone, quinhydrone, tannin, phenyl acetate, phenyl benzoate, 1-naphthyl acetate, 2-naphthyl acetate, phenyl chloracetate, hydroxyphenylalkanols, formaldehyde, paraformaldehyde, acetaldehyde, propanaldehyde, butyraldehyde, isobutyraldehyde, valeraldehyde, heptaldehyde, decanal, glyoxal, glutaraldehyde, terephthaldehyde, hexamethyl-enetetramine, trioxane, tetraoxane, polyoxymethylene, and divinylether may be used. Typical inorganic crosslinking agents are polyvalent metals, chelated polyvalent metals, and compounds capable of yielding polyvalent metals, including organometallic compounds as well as borates and boron complexes, and mixtures thereof. Preferred inorganic crosslinking agents include chromium salts, complexes, or chelates, such as chromium nitrate, chromium citrate, chromium acetate, chromium propionate, chromium malonate, chromium lactate, etc.; aluminum salts, such as aluminum citrate, aluminates, and aluminum complexes and chelates; titanium salts, complexes, and chelates; zirconium salts, complexes or chelates, such as zirconium lactate; and boron containing compounds such as boric acid, borates, and boron complexes. Fluids containing additives such as those described in U.S. Pat. Nos. 4,683,068 and 5,082,579 may be used.

As mentioned, the pre-gel fluid suspension formed in the invention may be foamed, normally by use of a suitable gas. Foaming procedures are well known, and per se form no part of the invention. In such instances, the fluids of the invention will preferably include a surfactant or surfactants. Preferred surfactants are water-soluble or dispersible and have sufficient foaming ability to enable the composition, when traversed or agitated by a gas, to foam. The selection of a suitable surface active agent or agents, is within the ability of those skilled in the art. Preferred surfactants are those which, when incorporated into water in a concentration of about 5 weight percent or less (based on the total weight of water and surfactant), meet the test described in the aforementioned U.S. Pat. No. 5,246,073, incorporated herein by reference.

Similarly, the precise nature of the proppant employed is not critical, the proppant being selected for the desired purpose, i.e., "propping" open a fracture, and those skilled in the art may readily select an appropriate wellbore particulate solid or solids for the desired purpose. The term "proppant" is understood to include mixtures, and may include, for example, a mixture of different sized proppants, or a gravel. Resin coated sand or ceramic proppant may be used. Particles or beads of silica, sintered materials or minerals, such as sintered bauxite, alumina, or corundum, may be used. Generally, the proppant will be added or present in the fluid in a concentration of from 0.5 or 1 lb./gallon to about 25 lbs/gallon, preferably from 1 lb./gallon to about 20 lbs/gallon. Normally, the proppant will have an average particle size less than about 8 mesh and greater than 60 or 80 mesh (U.S.). Sized mixtures of particles may be used, such as the common larger sized natural and synthetic inorganic proppant mixtures. Sized sand and synthetic inorganic proppants such as 20/40 sized sand, 16/20 sized sand, 12/20 sized sand, 8/12 sized sand, and similarly sized ceramic proppants, such as "CARBOLITE™" proppants, may be used.

The novel blend of aqueous suspending fluid, proppant, gellant, crosslinking agent, and organic polymeric particulate matter may be prepared, as indicated, in any suitable manner, the components being blended in any suitable sequence. Normally, however, the preferred job execution practice is to mix the entire batch to be pumped during the job. In some instances, it may be preferred to pump the suspension of the invention only during a portion of the job, e.g., as the last 10-25% of the proppant into the fracture as a "tail-in", to control flow back in the most economical manner or for other reasons. A slug may also be pumped at other stages. As mentioned, the invention has particular advantage in treatment of subterranean formations having a temperature above about 225° F.

In one procedural aspect of the invention, the fluid suspension is pumped down well, normally gelled, through the wellbore under fracturing pressure to the subterranean formation, and the subterranean formation may be fractured or the fracture may be extended. Gelling may be initiated or enhanced, for example, by temperature or by pH control, in a manner known to those skilled in the art. The gelled suspension is deposited in the formation, and after a suitable interval, such as after the fracturing operation is completed, the decomposition or reaction of the particulate matter in the downwell environment becomes significant. If necessary, the interval may be extended as appropriate to allow the gelled suspension to "break" or degrade. As used herein, the term "downwell environment" simply refers to the circumstances acting on the organic polymeric particulate matter downwell, including, but not limited to, the temperature of the subterranean formation, the composition of the formation, and any component or components of the suspension. Upon degradation of the gel by the action of the decomposition or reaction products, the fluids resulting from the breaking of the gel, minus leak-off, are then returned or allowed to return from the deposit locus to the wellbore, the decomposition or reaction of the solid particulate matter in effect "removing" organic polymeric particulate matter from the deposit. If additional particulate matter, such as durable fibers and/or platelets, or other materials are in the suspension deposited in the fracture, a matrix or pack of such and proppant (with a minor residuum of well treating fluid) is left in the fracture.

Suitable choline compounds for use in this invention include, without limitation, any choline salt. Exemplary examples include, without limitation, choline halides, choline sulfate, choline sulfite, choline phosphate, choline phosphite, choline carboxylates, or mixtures or combinations thereof. Exemplary examples of choline halides including choline fluoride, choline chloride, choline bromide, choline iodide, or mixtures or combinations thereof. Exemplary examples of choline carboxylates including, without limitation, choline formate, choline citrate, choline salicylate, choline propanate, similar choline carboxylates or mixtures or combinations thereof.

Suitable amines for use in the clay control compositions of this invention include, without limitation, di- and tri-alkyl substituted amines and mixtures or combinations thereof, where the alkyl groups include from 3 to 20 carbon atoms and/or hetero atoms. In certain embodiments, the clay control compounds can also include di-alkyl sulfides and di- and tri-alkyl phosphines where the alkyl groups include from 3 to 20 carbon atoms and/or hetero atoms.

Suitable ammonium salts for use in the clay control compositions of this invention include, without limitation, three general types of cationic materials: single-site cationic ammonium compounds, oligocationic ammonium compounds, and polycationic ammonium compounds and mixtures or combinations thereof. In certain embodiments, the clay control compound can also include phosphonium compounds and sulfonium compounds and mixtures or combinations thereof. Together the ammonium, phosphonium, and sulfonium compounds are sometimes referred to herein as "cationic formation control additives."

The single site amine and quaternaries useful as cationic formation control additives in my invention include di-, tri, and tetra-alkyl substituted amine and ammonium compounds wherein the alkyl groups include from 3 to 8 carbon atoms (Brown U.S. Pat. No. 2,761,835, incorporated herein by reference); substituted pyridine, pyridinium, morpholine and morphilinium compounds having from 1 to 6 carbon atoms in one or more substituent groups (Brown U.S. Pat. No. 2,761,840, incorporated herein by reference), additional heterocyclic nitrogen compounds such as histamine, imidazoles and substututed imidazoles, piperazines, piperidines, vinyl pyridines, and the like as described in Brown U.S. Pat. No. 2,761,836, incorporated herein by reference, the trialkylphenylammonium halides, dialkylmorpholinium halides and epihalohydrin derivatives described by Himes et al in the U.S. Pat. No. 4,842,073, incorporated herein by reference, and the allyl ammonium compounds of the formula $(CH_2{=}CHCH_2)_n N^+ (CH_3)_{4-n} X^-$; where $X^-$; is any anion which does not adversely react with the formation or the treatment fluid, described by Thomas and Smith in U.S. Pat. No. 5,211,239, incorporated herein by reference. In certain embodiments, the single site quaternaries are diallyl dimethyl ammonium chloride (DADMAC) (that is, the above formula where n=2 and $X^-$; is $Cl^-$;), and tetramethyl ammonium chloride, sometimes referred to as TMAC.

Oligocationics useful as cationic formation control additives in my invention include di- and polyamines (up to 100 nitrogens) substituted with alkyl groups having up to 12 carbon atoms (one or more of the nitrogens may be quaternized) as described by Brown in U.S. Pat. No. 2,761,843, incorporated herein by reference, and polyquaternaries described by Krieg in U.S. Pat. No. 3,349,032, incorporated herein by reference, namely alkyl aryl, and alkaryl bis- and polyquaternaries wherein two quaternary ammonium nitrogens are connected by various connecting groups having from 2-10 carbon atoms. In certain embodiments, the poly site quanternaries are poly DADMAC reagents as described in U.S. Pat. No. 6,921,742 to Smith, incorporated herein by reference.

Polyquaternary (cationic) formation control additives useful in my invention include those described by McLaughlin in the U.S. Pat. Nos. 4,366,071 and 4,374,739, incorporated herein by reference, namely polymers containing repeating groups having pendant quaternary nitrogen atoms wherein the quaternizing moieties are usually alkyl groups but which can include other groups capable of combining with the nitrogen and resulting in the quatemized state. I may also use any of the numerous polymers including quaternized nitrogen atoms which are integral to the polymer backbone, and other polymers having repeating quaternized units, as described in U.S. Pat. No. 4,447,342. Nitrogen-based cationic moieties may be interspersed with and/or copolymerized with up to 65% by weight (in certain embodiments, 1% to 65% by weight) nonionics such as acrylamide and even some anionics such as acrylic acid or hydrolyzed acrylamide. Molecular weights of the polymers may be quite high-up to a million or more. Such copolymers are included in my definition of polycationic formation control additives useful in my invention.

In certain embodiments, the anions for association with the quaternized nitrogen atoms are halide anions, such as chloride ions, that readily dissociate in the aqueous drilling or other formation treatment fluid, but any anions, including formate anions, may be used which will not interfere with the purposes of the formation treatment. Persons skilled in the art may wish to review the various anions mentioned in the above incorporated patents.

Thus, it is seen that a cationic formation control additive useful in my invention is a material having from one to hundreds or thousands of cationic sites, generally either amines or quaternized amines, but may include other cationic or quaternized sites such as phosphonium or sulfonium groups.

In the present invention, the inventor employs a choline compound and an amine, phosphine or sulfide and/or a cationic formation control additive with or without a formate salt such as potassium formate. The choline compound and the formate compound may be added to the formation treating or drilling fluid before or after the amine, phosphine or sulfide and/or cationic formation control additive. The potassium formate may be added to the formation treating or drilling fluid before or after the cationic formation control additive, or may be made in situ by the reaction of potassium hydroxide and formic acid. The potassium hydroxide and formic acid may be added in any order, separately or together, before or after the addition of the cationic formation control additive, and need not be added in exact molar proportions. Any effective amount of the combination of a choline compound and formation control additives (amines, phosphines, or sulfides and/or cationic formation control additives) may be used, but in certain embodiments, the ratios of a choline compound to formation control additive with or without potassium formate of 25:75 to 75:25 by weight in the solution, in combined concentrations of at least 0.001% by weight in the drilling or other formation treatment fluid. In certain embodiments, the additive package to the fluid is between about 0.05 wt. % and about 5 wt. %.

Suitable Reagents

Suitable hydrocarbon base fluids for use in this invention includes, without limitation, synthetic hydrocarbon fluids, petroleum based hydrocarbon fluids, natural hydrocarbon (non-aqueous) fluids, those fluids described in United States Published Application No. 20050189911, incorporated herein by reference, or other similar hydrocarbons or mixtures or combinations thereof. The hydrocarbon fluids for use in the present invention have viscosities ranging from about $0.5 \times 10^{-6}$ to about $600 \times 10^{-6}$ m$^2$/s (0.5 to about 600 centistokes). Exemplary examples of such hydrocarbon fluids include, without limitation, polyalphaolefins, polybutenes, polyolesters, biodiesels, simple low molecular weight fatty esters of vegetable or vegetable oil fractions, simple esters of alcohols such as Exxate from Exxon Chemicals, vegetable oils, animal oils or esters, other essential oil, diesel having a low or high sulfur content, kerosene, jet-fuel, white oils, mineral oils, mineral seal oils, hydrogenated oil such as PetroCanada HT-40N or IA-35 or similar oils produced by Shell Oil Company, internal olefins (IO) having between about 12 and 20 carbon atoms, linear alpha olefins having between about 14 and 20 carbon atoms, polyalpha olefins having between about 12 and about 20 carbon atoms, isomerized alpha olefins (IAO) having between about 12 and about 20 carbon atoms, VM&P Naptha, Linpar, Parafins having between 13 and about 16 carbon atoms, and mixtures or combinations thereof.

Suitable polyalphaolefins (PAOs) include, without limitation, polyethylenes, polypropylenes, polybutenes, polypentenes, polyhexenes, polyheptenes, higher PAOs, copolymers thereof, and mixtures thereof. Exemplary examples of PAOs include PAOs sold by Mobil Chemical Company as SHF fluids and PAOs sold formerly by Ethyl Corporation under the name ETHYLFLO and currently by Albemarle Corporation under the trade name Durasyn. Such fluids include those specified as ETYHLFLO 162, 164, 166, 168, 170, 174, and 180. Well suited PAOs for use in this invention include bends of about 56% of ETHYLFLO now Durasyn 174 and about 44% of ETHYLFLO now Durasyn 168.

Exemplary examples of polybutenes include, without limitation, those sold by Amoco Chemical Company and Exxon Chemical Company under the trade names INDOPOL and PARAPOL, respectively. Well suited polybutenes for use in this invention include Amoco's INDOPOL 100.

Exemplary examples of polyolester include, without limitation, neopentyl glycols, trimethylolpropanes, pentaerythritols, dipentaerythritols, and diesters such as dioctylsebacate (DOS), diactylazelate (DOZ), and dioctyladipate.

Exemplary examples of petroleum based fluids include, without limitation, mineral spirits, white mineral oils, paraffinic oils, and medium-viscosity-index (MVI) naphthenic oils having viscosities ranging from about $0.5 \times 10^{-6}$ to about $600 \times 10^{-6}$ m$^2$/s (0.5 to about 600 centistokes) at 40° C. Exemplary examples of mineral spirits include those sold by SynOil Fluids under trade names SF-840, SF-800, SF-770 and TG-740, BPAmoco under trade names Buck Creek and C2000, and Enerchem under trade name Fracsol. Exemplary examples of white mineral oils include those sold by Witco Corporation, Arco Chemical Company, PSI, and Penreco. Exemplary examples of paraffinic oils include solvent neutral oils available from Exxon Chemical Company, high-viscosity-index (HVI) neutral oils available from Shell Chemical Company, and solvent treated neutral oils available from Arco Chemical Company. Exemplary examples of MVI naphthenic oils include solvent extracted coastal pale oils available from Exxon Chemical Company, MVI extracted/acid treated oils available from Shell Chemical Company, and naphthenic oils sold under the names HydroCal and Calsol by Calumet and hydrogenated oils such as HT-40N and IA-35 from PetroCanada or Shell Oil Company or other similar hydrogenated oils.

Exemplary examples of vegetable oils include, without limitation, castor oils, corn oil, olive oil, sunflower oil, sesame oil, peanut oil, palm oil, palm kernel oil, coconut oil, butter fat, canola oil, rape seed oil, flax seed oil, cottonseed oil, linseed oil, other vegetable oils, modified vegetable oils such as crosslinked castor oils and the like, and mixtures thereof. Exemplary examples of animal oils include, without limitation, tallow, mink oil, lard, other animal oils, and mixtures thereof. Other essential oils will work as well. Of course, mixtures of all the above identified oils can be used as well. Crude oils, Gas Condensates, Liquified Petroleum Gasses, and blends or mixtures of all the above will work with present invention in the presence of Nitrogen gas, and or Carbon Dioxide gas or liquid.

Suitable other gelling agents for use in this invention include, without limitation, any gelling agent. Exemplary gelling agents includes ethylene-acrylic acid copolymer, ethylene-methacrylic acid copolymers, ethylene-vinyl acetate copolymers, ethylene-maleic anhydride copolymers, butadiene-methacrylic acid copolymers, ethylene-methacrylic acid copolymers, styrene-butadiene-acrylic acid copolymers, styrene-butadiene-methacrylic acid copolymers, or other copolymer including monomers having acid moieties or mixtures or combinations thereof. Exemplary examples phosphate ester gelling agents of this invention include, without limitation, variants of the phosphate esters WEC HGA 37, WEC HGA 70, WEC HGA 71, WEC HGA 72, WEC HGA 702 or mixtures or combinations thereof using tri-alkyl-phosphates in place of tri-ethyl-phosphate, available from Weatherford International iso-octyl, 2-ethylhexyl, phosphate esters or other phosphate esters from P-2, and similar phosphonate esters of high molecular weight alcohols available from Halliburton or mixtures or combinations thereof. Other suitable gelling agents include, without limitation, Geltone II available from Baroid, Ken-Gel available from Imco or the like.

Suitable cross-linking agent for use in this invention include, without limitation, any suitable cross-linking agent for use with the gelling agents. Exemplary cross-linking agents include, without limitation, di-, tri or tetra-valent metal salts such as calcium salts, magnesium salts, cerium salts, barium salts, copper (copprous and cupric) salts, cobalt salts, chromium salts, manganese salts, titanium salts, iron salts (ferrous and ferric), zinc salts, zirconium salts, aluminum salts, any other transition metal, actinide metal or lanthanide metal salt capable of acting as a phosphate ester cross-linking agent or mixtures or combinations thereof. Exemplary examples cross-linking agent for use with phosphate esters include, without limitation, WEC HGA 44, WEC HGA 44AX, WEC HGA 48, WEC HGA 55se, WEC HGA 55s, WEC HGA 61, WEC HGA Super 61, WEC HGA 65 or mixtures or combinations thereof available from Weatherford International.

EXPERIMENTS OF THE INVENTION

Preparation of Compositions

Example 1

This example illustrates the preparation of a preferred phosphate ester for use in oil field fluids of this invention, where the phosphate ester is derived from tri-butyl-phosphate. The phosphate ester was prepared using the following wt. % of ingredients.

| Ingredient | wt. % |
| --- | --- |
| Tributyl-Phosphate (TBP) | 43.87 |
| Phosphorus Pentoxide ($P_2O_5$) | 13.38 |
| Alfol 810 Alcohol | 42.75 |

The TBP was added to a clean reaction vessel. The mixer was turned on and the vessel was purged with nitrogen gas and blanketed with nitrogen gas. The phosphorus pentoxide was then added incrementally to the vessel. The starting time and temperature were recorded. After the phosphorous pentoxide was added, the reaction was allowed to proceed and the final time and temperature were recorded. The reaction exothermed to a temperature between 240° F. and 250° F. If the temperature does not reach a temperature between 240° F. and 250° F., then the reaction mixtures is heated to a temperature within this range. While in commercial equipment, no heat is generally needed, in all laboratory testing, heat was required to reach a final temperature between 240° F. and 250° F. The reaction mixtures were held at a temperature between 240° F. and 250° F. for 2 hours after the final addition of phosphorous pentoxide. The hold time can be started as the reaction is being heated to the required temperature providing that the hold temperature is reached within a 30 minute time frame. After the hold time, the Alfol 810 Alcohol (C8-C10 mixture of alcohols available from Sasol) was added, which caused a reaction exotherm to a max temp of about 300° F. The reaction mixtures was held at a temperature between 250° F. and 260° F. for 4 hours or until required QC acid values are reached. The reaction was run at three different batch sizes 1 L (Example 1a), 5 L (Example 1b) and 22 L (Example 1c). The final product physical properties are tabulated in Table I.

TABLE I

| Physical Properties | |
| --- | --- |
| Appearance | Clear yellow to amber/brown liquid |
| Specific Gravity @ 25C | 0.99741 |
| Density (lb/gal) | 8.3124 |
| wt. % Water | 359.11 ppm |
| pH (50/50) | 1.60 |
| Acid Value @ pH 5-5.5 | 199.4 |
| Acid Value @ pH 9-9.5 | 243.2 |
| Marsh Funnel (Test as RG-20 with RG21 at 1%) | 3:10 minutes |
| Freeze point | −15° C. |
| Flash Point | >212° F. |

Example 2a

This example illustrates the preparation of a variant of HGA 70 prepared using the phosphate ester of Example 1a using the wt. % of ingredients listed below.

| Ingredient | wt. % |
| --- | --- |
| Example 1a | 71 |
| Caustic Potash 45% | 19 |
| Solvent 142 HT, Aliphatic Solvent | 10.04 |

The ingredients were added to a vessel with mixing. Although the order of addition is immaterial, the solvent is generally added first.

Example 2b

This example illustrates the preparation of a variant of HGA 70 prepared using the phosphate ester of Example 1b using the wt. % of ingredients listed below.

| Ingredient | wt. % |
| --- | --- |
| Example 1b | 71 |
| Caustic Potash 45% | 19 |
| Solvent 142 HT, Aliphatic Solvent | 10.04 |

The ingredients were added to a vessel with mixing. Although the order of addition is immaterial, the solvent is generally added first.

Example 2c

This example illustrates the preparation of a variant of HGA 70 prepared using the phosphate ester of Example 1c using the wt. % of ingredients listed below.

| Ingredient | wt. % |
| --- | --- |
| Example 1c | 71 |
| Caustic Potash 45% | 19 |
| Solvent 142 HT, Aliphatic Solvent | 10.04 |

The ingredients were added to a vessel with mixing. Although the order of addition is immaterial, the solvent is generally added first.

Comparative Example 3

This example illustrates the preparation of an embodiment of an oilfield fluid of this invention using equal amount of HGA 65 and HGA 70, available from Weatherford International in low sulfur lab diesel.

To 100 mL of low sulfur lab diesel was added 0.8 vol. % of HGA 70, a phosphate ester available from Weatherford International made with tri-ethyl-phosphate, and 0.8 vol. % of HGA 65, a cross-linking agent available form Weatherford International. The resulting solution was mixed for 1 minute on Hamilton Beach Mixer at the highest speed.

Example 3a

This example illustrates the preparation of an embodiment of an oilfield fluid of this invention using equal amounts of HGA 65 available from Weatherford International and the HGA 70 variant Example 2a in low sulfur lab diesel.

To 100 mL of low sulfur lab diesel was added 0.8 vol. % of Example 2a and 0.8 vol. % of HGA 65, a cross-linking agent available form Weatherford International. The resulting solution was mixed for 1 minute on Hamilton Beach Mixer at the highest speed.

Example 3b

This example illustrates the preparation of an embodiment of an oilfield fluid of this invention using equal amounts of HGA 65 available from Weatherford International and the HGA 70 variant Example 2b in low sulfur lab diesel.

To 100 mL of low sulfur lab diesel was added 0.8 vol. % of Example 2b, and 0.8 vol. % of HGA 65, a cross-linking agent available form Weatherford International. The resulting solution was mixed for 1 minute on Hamilton Beach Mixer at the highest speed.

Example 3c

This example illustrates the preparation of an embodiment of an oilfield fluid of this invention using equal amounts of HGA 65 available from Weatherford International and the HGA 70 variant Example 2c in low sulfur lab diesel.

To 100 mL of low sulfur lab diesel was added 0.8 vol. % of Example 2c and 0.8 vol. % of HGA 65, a cross-linking agent available form Weatherford International. The resulting solution was mixed for 1 minute on Hamilton Beach Mixer at the highest speed.

Example 4a

This example illustrates the preparation of a variant of HGA 37 prepared using the phosphate ester of Example 1a using the wt. % of ingredients listed below.

| Ingredient | wt. % |
| --- | --- |
| Example 1a | 73.65 |
| KOH (50%) | 13.6 |
| Water | 1.69 |
| Solvent 142 HT, Aliphatic Solvent | 10.63 |

The ingredients were added to a vessel with mixing. Although the order of addition is immaterial, the solvent is generally added first.

Example 4b

This example illustrates the preparation of a variant of HGA 37 prepared using the phosphate ester of Example 1b using the wt. % of ingredients listed below.

| Ingredient | wt. % |
| --- | --- |
| Example 1b | 73.65 |
| KOH (50%) | 13.6 |
| Water | 1.69 |
| Solvent 142 HT, Aliphatic Solvent | 10.63 |

The ingredients were added to a vessel with mixing. Although the order of addition is immaterial, the solvent is generally added first.

Example 4c

This example illustrates the preparation of a variant of HGA 37 prepared using the phosphate ester of Example 1c using the wt. % of ingredients listed below.

| Ingredient | wt. % |
| --- | --- |
| Example 1c | 73.65 |
| KOH (50%) | 13.6 |
| Water | 1.69 |
| Solvent 142 HT, Aliphatic Solvent | 10.63 |

The ingredients were added to a vessel with mixing. Although the order of addition is immaterial, the solvent is generally added first.

Comparative Example 5

This example illustrates the preparation of an embodiment of an oilfield fluid of this invention using equal amount of HGA 44 and HGA 37, available from Weatherford International in low sulfur lab diesel.

To 100 mL of low sulfur lab diesel was added 0.8 vol. % of HGA 37, a phosphate ester available from Weatherford International made with tri-ethyl-phosphate, and 0.8 vol. % of HGA 44, a cross-linking agent available form Weatherford International. The resulting solution was mixed for 1 minute on Hamilton Beach Mixer at the highest speed.

Example 5a

This example illustrates the preparation of an embodiment of an oilfield fluid of this invention using equal amounts of HGA 44 available from Weatherford International and the HGA 37 variant Example 4a in low sulfur lab diesel.

To 100 mL of low sulfur lab diesel was added 0.8 vol. % of Example 4a and 0.8 vol. % of HGA 44, a cross-linking agent available form Weatherford International. The resulting solution was mixed for 1 minute on Hamilton Beach Mixer at the highest speed.

Example 5b

This example illustrates the preparation of an embodiment of an oilfield fluid of this invention using equal amounts of HGA 44 available from Weatherford International and the HGA 37 variant Example 4b in low sulfur lab diesel.

To 100 mL of low sulfur lab diesel was added 0.8 vol. % of Example 4b and 0.8 vol. % of HGA 44, a cross-linking agent available form Weatherford International. The resulting solution was mixed for 1 minute on Hamilton Beach Mixer at the highest speed.

Example 5c

This example illustrates the preparation of an embodiment of an oilfield fluid of this invention using equal amounts of HGA 44 available from Weatherford International and the HGA 37 variant Example 4c in low sulfur lab diesel.

To 100 mL of low sulfur lab diesel was added 0.8 vol. % of Example 4c and 0.8 vol. % of HGA 44, a cross-linking agent available form Weatherford International. The resulting solution was mixed for 1 minute on Hamilton Beach Mixer at the highest speed.

Comparative Example 6

This example illustrates the preparation of an embodiment of an oilfield fluid of this invention using equal amount of HGA Super 61 and HGA 70, available from Weatherford International in low sulfur lab diesel.

To 100 mL of low sulfur lab diesel was added 0.8 vol. % of HGA 70, a phosphate ester available from Weatherford International made with tri-ethyl-phosphate, and 0.8 vol. % of HGA Super 61, a cross-linking agent available form Weatherford International. The resulting solution was mixed for 1 minute on Hamilton Beach Mixer at the highest speed.

Example 6a

This example illustrates the preparation of an embodiment of an oilfield fluid of this invention using equal amounts of HGA Super 61 available from Weatherford International and the HGA 70 variant Example 2a in low sulfur lab diesel.

To 100 mL of low sulfur lab diesel was added 0.8 vol. % of Example 2a and 0.8 vol. % of HGA Super 61, a cross-linking agent available form Weatherford International. The resulting solution was mixed for 1 minute on Hamilton Beach Mixer at the highest speed.

Example 6b

This example illustrates the preparation of an embodiment of an oilfield fluid of this invention using equal amounts of HGA Super 61 available from Weatherford International and the HGA 70 variant Example 2b in low sulfur lab diesel.

To 100 mL of low sulfur lab diesel was added 0.8 vol. % of Example 2b and 0.8 vol. % of HGA Super 61, a cross-linking agent available form Weatherford International. The resulting solution was mixed for 1 minute on Hamilton Beach Mixer at the highest speed.

Example 6c

This example illustrates the preparation of an embodiment of an oilfield fluid of this invention using equal amounts of HGA Super 61 available from Weatherford International and the HGA 70 variant Example 2c in low sulfur lab diesel.

To 100 mL of low sulfur lab diesel was added 0.8 vol. % of Example 2c and 0.8 vol. % of HGA Super 61, a cross-linking agent available form Weatherford International. The resulting solution was mixed for 1 minute on Hamilton Beach Mixer at the highest speed.

Example 7a

This example illustrates the preparation of a variant of HGA 715 prepared using the phosphate ester of Example 1a using the wt. % of ingredients listed below.

| Ingredient | wt. % |
| --- | --- |
| Example 1a | 71 |
| Caustic Potash 45% | 19 |
| Solvent 142 HT, Aliphatic Solvent | 10.04 |

The ingredients were added to a vessel with mixing. Although the order of addition is immaterial, the solvent is generally added first.

Example 7b

This example illustrates the preparation of a variant of HGA 715 prepared using the phosphate ester of Example 1b using the wt. % of ingredients listed below.

| Ingredient | wt. % |
| --- | --- |
| Example 1b | 71 |
| Caustic Potash 45% | 19 |
| Solvent 142 HT, Aliphatic Solvent | 10.04 |

The ingredients were added to a vessel with mixing. Although the order of addition is immaterial, the solvent is generally added first.

Example 7c

This example illustrates the preparation of a variant of HGA 715 prepared using the phosphate ester of Example 1c using the wt. % of ingredients listed below.

| Ingredient | wt. % |
| --- | --- |
| Example 1c | 71 |
| Caustic Potash 45% | 19 |
| Solvent 142 HT, Aliphatic Solvent | 10.04 |

The ingredients were added to a vessel with mixing. Although the order of addition is immaterial, the solvent is generally added first.

Comparative Example 8

This example illustrates the preparation of an embodiment of an oilfield fluid of this invention using equal amount of HGA 44AX and HGA 715, available from Weatherford International in low sulfur lab diesel.

To 100 mL of low sulfur lab diesel was added 0.8 vol. % of HGA 715, a phosphate ester available from Weatherford International made with tri-ethyl-phosphate, and 0.8 vol. % of HGA 44AX, a cross-linking agent available form Weatherford International. The resulting solution was mixed for 1 minute on Hamilton Beach Mixer at the highest speed.

Example 8a

This example illustrates the preparation of an embodiment of an oilfield fluid of this invention using equal amounts of HGA 44AX available from Weatherford International and the HGA 715 variant Example 7a in low sulfur lab diesel.

To 100 mL of low sulfur lab diesel was added 0.8 vol. % of Example 7a and 0.8 vol. % of HGA 44AX, a cross-linking agent available form Weatherford International. The resulting solution was mixed for 1 minute on Hamilton Beach Mixer at the highest speed.

Example 8b

This example illustrates the preparation of an embodiment of an oilfield fluid of this invention using equal amounts of HGA 44AX available from Weatherford International and the HGA 715 variant Example 7b in low sulfur lab diesel.

To 100 mL of low sulfur lab diesel was added 0.8 vol. % of Example 7b and 0.8 vol. % of HGA 44AX, a cross-linking agent available form Weatherford International. The resulting solution was mixed for 1 minute on Hamilton Beach Mixer at the highest speed.

Example 8c

This example illustrates the preparation of an embodiment of an oilfield fluid of this invention using equal amounts of HGA 44AX available from Weatherford International and the HGA 715 variant Example 7c in low sulfur lab diesel.

To 100 mL of low sulfur lab diesel was added 0.8 vol. % of Example 7c, and 0.8 vol. % of HGA 44AX, a cross-linking agent available form Weatherford International. The resulting solution was mixed for 1 minute on Hamilton Beach Mixer at the highest speed.

Comparative Example 9

This example illustrates the preparation of an embodiment of an oilfield fluid of this invention using equal amount of HGA 61 and HGA 70, available from Weatherford International in low sulfur lab diesel.

To 100 mL of low sulfur lab diesel was added 0.8 vol. % of HGA 70, a phosphate ester available from Weatherford International made with tri-ethyl-phosphate, and 0.8 vol. % of HGA 61, a cross-linking agent available form Weatherford International. The resulting solution was mixed for 1 minute on Hamilton Beach Mixer at the highest speed.

Example 9a

This example illustrates the preparation of an embodiment of an oilfield fluid of this invention using equal amounts of HGA 61 available from Weatherford International and the HGA 70 variant Example 2a in low sulfur lab diesel.

To 100 mL of low sulfur lab diesel was added 0.8 vol. % of Example 2a, and 0.8 vol. % of HGA 61, a cross-linking agent available form Weatherford International. The resulting solution was mixed for 1 minute on Hamilton Beach Mixer at the highest speed.

Example 9b

This example illustrates the preparation of an embodiment of an oilfield fluid of this invention using equal amounts of HGA 61 available from Weatherford International and the HGA 70 variant Example 2b in low sulfur lab diesel.

To 100 mL of low sulfur lab diesel was added 0.8 vol. % of Example 2b and 0.8 vol. % of HGA 61, a cross-linking agent available form Weatherford International. The resulting solution was mixed for 1 minute on Hamilton Beach Mixer at the highest speed.

Example 9c

This example illustrates the preparation of an embodiment of an oilfield fluid of this invention using equal amounts of HGA 61 available from Weatherford International and the HGA 70 variant Example 2c in low sulfur lab diesel.

To 100 mL of low sulfur lab diesel was added 0.8 vol. % of Example 2c, and 0.8 vol. % of HGA 61, a cross-linking agent available form Weatherford International. The resulting solution was mixed for 1 minute on Hamilton Beach Mixer at the highest speed.

Comparative Example 10

This example illustrates the preparation of an embodiment of an oilfield fluid of this invention using equal amount of HGA 48 and HGA 37, available from Weatherford International in low sulfur lab diesel.

To 100 mL of low sulfur lab diesel was added 0.8 vol. % of HGA 37, a phosphate ester available from Weatherford International made with tri-ethyl-phosphate, and 0.8 vol. % of HGA 48, a cross-linking agent available form Weatherford International. The resulting solution was mixed for 1 minute on Hamilton Beach Mixer at the highest speed.

Example 10a

This example illustrates the preparation of an embodiment of an oilfield fluid of this invention using equal amounts of HGA 48 available from Weatherford International and the HGA 37 variant Example 4a in low sulfur lab diesel.

To 100 mL of low sulfur lab diesel was added 0.8 vol. % of Example 4a, and 0.8 vol. % of HGA 48, a cross-linking agent available form Weatherford International. The resulting solution was mixed for 1 minute on Hamilton Beach Mixer at the highest speed.

Example 10b

This example illustrates the preparation of an embodiment of an oilfield fluid of this invention using equal amounts of HGA 48 available from Weatherford International and the HGA 37 variant Example 4b in low sulfur lab diesel.

To 100 mL of low sulfur lab diesel was added 0.8 vol. % of Example 4b and 0.8 vol. % of HGA 48, a cross-linking agent available form Weatherford International. The resulting solution was mixed for 1 minute on Hamilton Beach Mixer at the highest speed.

Example 10c

This example illustrates the preparation of an embodiment of an oilfield fluid of this invention using equal amounts of HGA 44 available from Weatherford International and the HGA 37 variant Example 4c in low sulfur lab diesel.

To 100 mL of low sulfur lab diesel was added 0.8 vol. % of Example 4c, and 0.8 vol. % of HGA 48, a cross-linking agent available form Weatherford International. The resulting solution was mixed for 1 minute on Hamilton Beach Mixer at the highest speed.

Testing of Compositions

Test Method

The composition set forth above were tested using a test method developed by Canadian Crude Quality Technical Association. The method determines volatile organo-phosphorus compounds in volatile distillates of crude oil by inductively coupled plasma atomic emission (ICP) Spectrometry. The test method is described below.

Sample Testing

A weighed sub-sample of a thoroughly homogenized crude oil sample is distilled at ambient pressure using a conventional petroleum distillation apparatus (consisting of a thermometer, distillation flask, condenser, cooling bath and a receiving cylinder.) The distillation is performed under conditions to provide a distillate fraction collected from the initial boiling point (IBP) to 250° C. The analytical solution is prepared by mixing the fraction with an organic solvent. Calibration standards are prepared in the same solvent. An internal standard is added to the solutions to compensate for variations in test specimen introduction efficiency. The solutions are nebulized into the plasma of the Inductively Coupled Plasma Atomic Emission Spectrometry (ICP) instrument, and the intensities of the emitted light at wavelengths characteristic of phosphorus are measured. By comparing the emission intensities of the element in the test solution with emission intensities of the calibration standards, and by applying the appropriate internal standard correction, the concentration of elements in the test sample are calculated.

Standards and Samples Preparation

Blank—Prepare a blank by diluting mineral oil with dilution solvent.

Test Sample—Distill a well-homogenized crude oil sample and retain the distillate fraction from IBP to 250° C., as described in ASTM D 86. Weigh a portion of the well-mixed distillate to the nearest 0.001 g, into a container and add sufficient solvent to achieve a suitable sample concentration within the linear range of calibration of the ICP.

Check Standard—Weigh to the nearest 0.001 g, a portion of the organo-metallic standard into a container and add sufficient dilution solvent to achieve a suitable analyte concentration of approximately the same as expected in the test sample.

Working Standard—Weigh to the nearest 0.001 g, a portion of the pre-prepared organo-metallic standard into a suitable container and dilute with an appropriate amount of dilution solvent. More than one working standard can be prepared at higher or lower final concentrations to bracket the expected concentration of analyte in the test sample.

Internal Standard (IS)—. The concentration of the internal standard is not required to be a set value. However, the IS must be added in a consistent manner to all solutions (test samples, blanks, check standards, working standards and QC standard solutions).

Record all weights and calculate dilution factors.

Calibration

The linear range for the instrument must be established for the operating parameter.

Working Standards—At the beginning of each analytical batch of test samples, perform a multi-point calibration, consisting of the blank and one or more working standards. Analyze the check standard to verify if the element is within calibration. Proceed with the test sample analyses if the check standard is within 5% relative percent difference (RPD) of its true value. Otherwise, make the necessary adjustments to the instrument or rerun the working standards.

Working Standard with Internal Standard—Calibrate the instrument as described in 10.2. Calculate an intensity ratio for the element by the following equation:

$$I(Re) + (I(e) - I(Be))/I(is) \tag{1}$$

where I(Re) is the intensity ratio for element e, I(e) is intensity for element e, I(Be) is the intensity of the blank for element e, and I(is) is the intensity of internal standard element.

Calculate the calibration factors from the intensity ratios. Alternatively, use the ICP software as provided by the instrument manufacturer to calibrate the instrument using internal standardization.

Procedure

Analyze the test samples in the same manner as the calibration standards Between test samples, nebulize dilution solvent. When the concentration in any test sample exceeds the linear range of calibration, prepare another test solution with a higher dilution.

Analyze the check standard after a maximum of every tenth test specimen solution. If any result is not within 5% RPD of the expected concentration, recalibrate the instrument and reanalyze the test samples back to the previously accepted check standard.

Calculation and Reporting

Calculate the analyte concentration, using the following equation:

$$C = S \times (W1 + W2)/W1 \tag{2}$$

where C is the calculated analyte concentration in the sample, S is the analyte concentration in the test sample, W1 is the sample mass in grams, and W2 is the diluent mass in grams. In most instances, the ICP software automatically performs this calculation, in addition to calculating the intensity ratio using Equation 1 above.

Report the result in mg/kg to three significant figures as the total phosphorus content in the volatile fraction of the crude oil sample.

Test Results

The results of volatile phosphate test for the compositions of Comparative Examples 3-10 and Examples 3a-10c are tabulated in following tables.

TABLE II

Volatile Phosphorus Testing for Example 3 Compositions

| Compound | Volatile Phosphorus Value |
|---|---|
| Comparative Example 3 | 212.8 |
| Example 3a | 26.81 |
| Example 3b | 0.0 |
| Example 3c | 0.0 |

TABLE III

Volatile Phosphorus Testing for Example 3 Compositions

| Compound | Volatile Phosphorus Value |
|---|---|
| Comparative Example 5 | 86.04 |
| Example 5a | 4.964 |
| Example 5b | 0.0 |
| Example 5c | 0.0 |

TABLE IV

Volatile Phosphorus Testing for Example 3 Compositions

| Compound | Volatile Phosphorus Value |
| --- | --- |
| Comparative Example 6 | 159.8 |
| Example 6a | 55.16 |
| Example 6b | 0.0 |
| Example 6c | 0.0 |

TABLE V

Volatile Phosphorus Testing for Example 3 Compositions

| Compound | Volatile Phosphorus Value |
| --- | --- |
| Comparative Example 8 | 127.6 |
| Example 8a | 10.47 |
| Example 8b | 0.0 |
| Example 8c | 0.0 |

TABLE VI

Volatile Phosphorus Testing for Example 3 Compositions

| Compound | Volatile Phosphorus Value |
| --- | --- |
| Comparative Example 9 | 175.3 |
| Example 9a | 23.12 |
| Example 9b | 0.0 |
| Example 9c | 0.0 |

TABLE VII

Volatile Phosphorus Testing for Example 3 Compositions

| Compound | Volatile Phosphorus Value |
| --- | --- |
| Comparative Example 10 | 146.6 |
| Example 10a | 5.308 |
| Example 10b | 0.0 |
| Example 10c | 0.0 |

It is apparent that the compositions prepared using a phosphate ester derived from tri-butyl-phosphate (TBP) showed significantly lower volatile phosphorus values. It is also clear that the laboratory prepared phosphate ester derived from TBP have a significantly higher volatile phosphorus value than the scaled up versions of the same phosphate ester. In fact, based on the test data, the scaled up version of all the compositions from Examples 3a-10c have no detectable volatile phosphorus.

Referring now to FIG. 1, a plot of the viscosity of the composition of Examples 3a-c versus temperature shows that the viscosity of the composition of Examples 3a-c breaks with increasing temperature, a key features of a good fracturing fluid.

Figure 2:
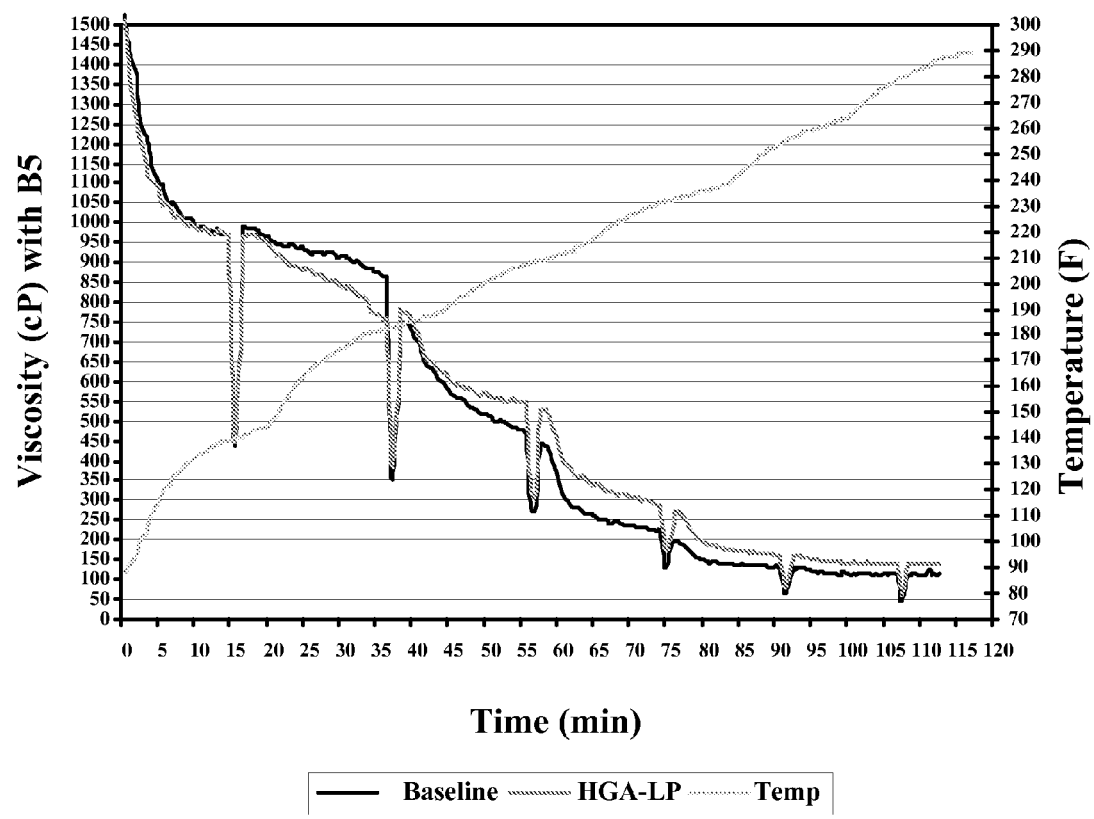
FIG. 2 is a plot depicting the viscosity verses temperature behavior of another fluid embodiment of this invention.

Referring now to FIG. 2, a plot of the viscosity of the composition of Example 5a-c versus temperature shows that the viscosity of the composition of Examples 3a-c breaks with increasing temperature, a key features of a good fracturing fluid.

Figure 3:
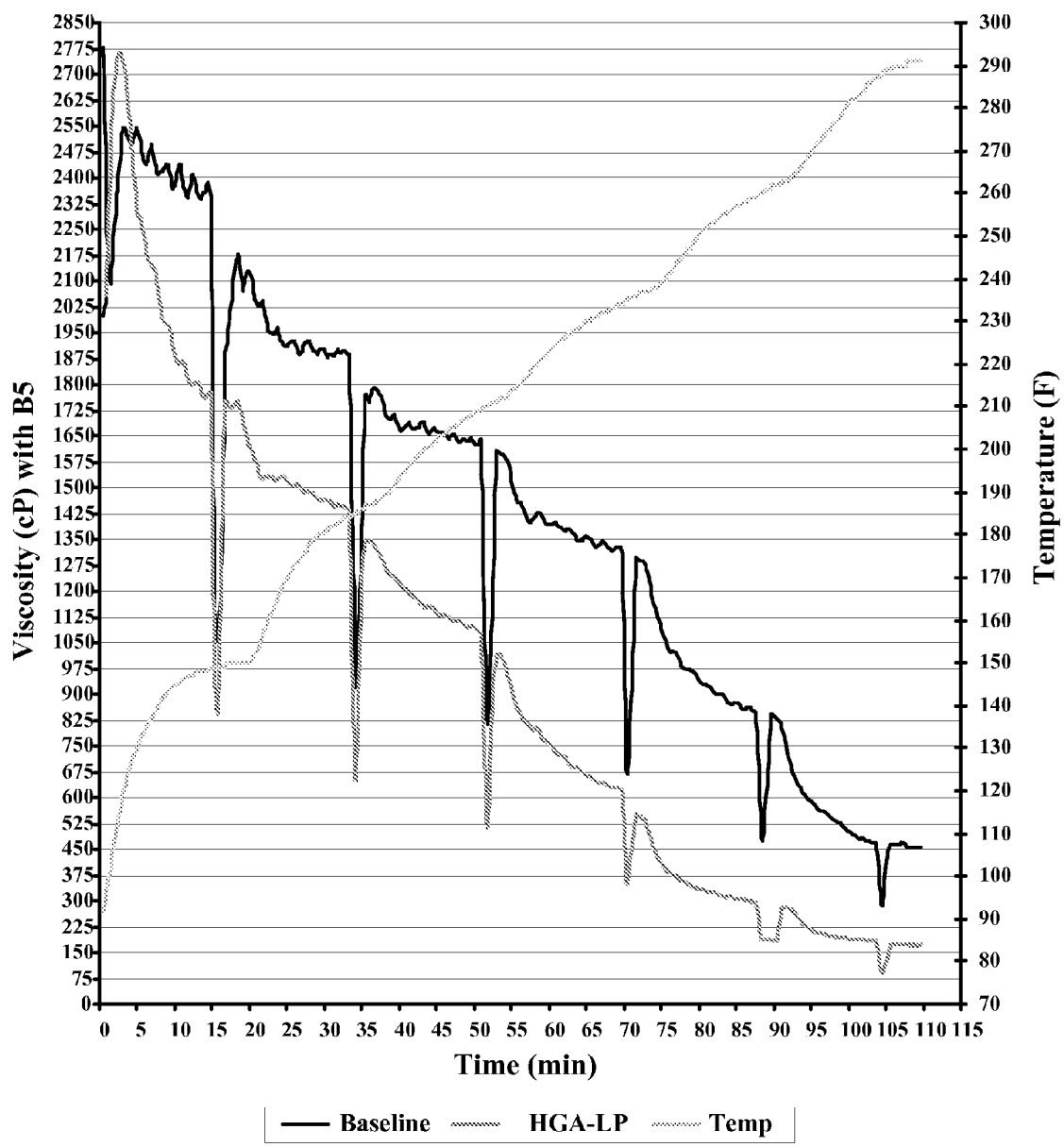
FIG. 3 is a plot depicting the viscosity verses temperature behavior of another fluid embodiment of this invention.

Referring now to FIG. 3, a plot of the viscosity of the composition of Example 6a-c versus temperature shows that the viscosity of the composition of Examples 3a-c breaks with increasing temperature, a key features of a good fracturing fluid.

Figure 4:
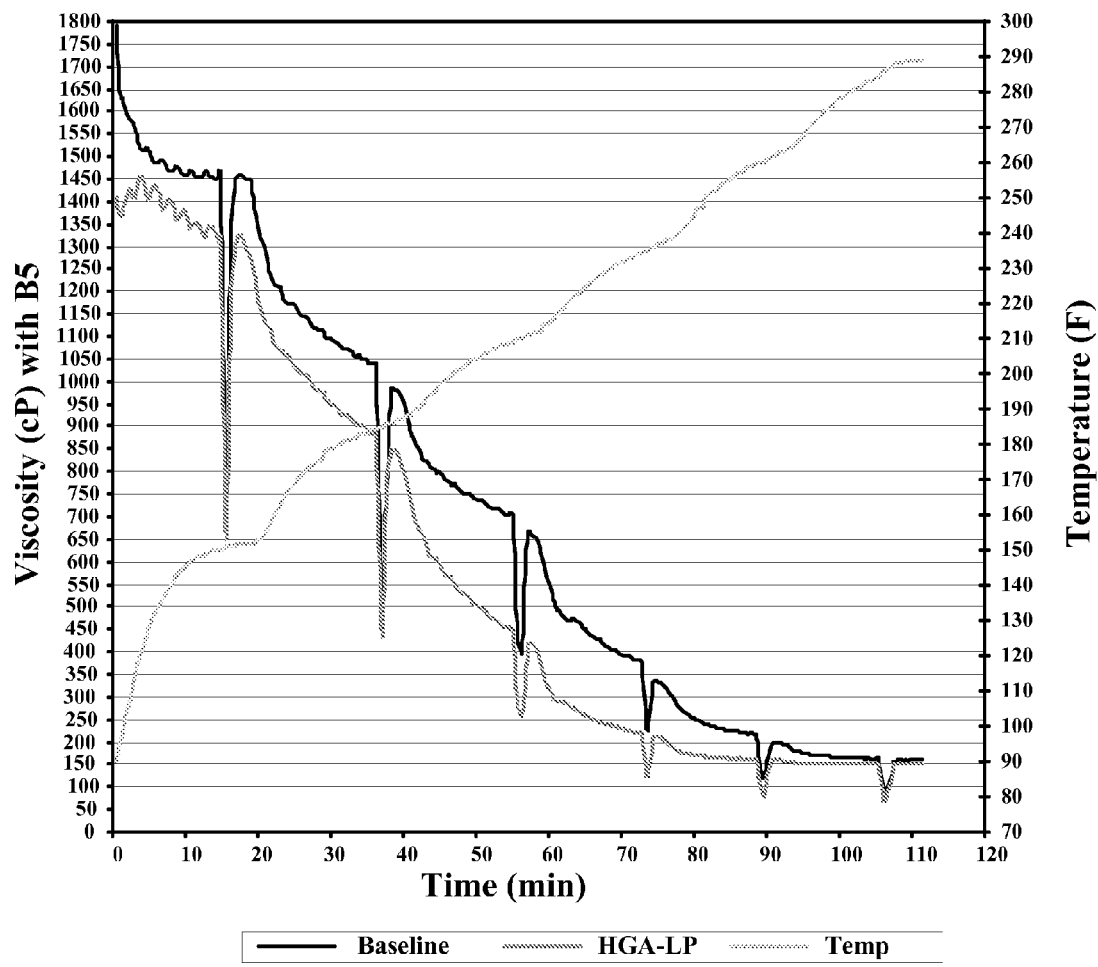
FIG. 4 is a plot depicting the viscosity verses temperature behavior of another fluid embodiment of this invention.

Referring now to FIG. 4, a plot of the viscosity of the composition of Example 8a-c versus temperature shows that the viscosity of the composition of Examples 3a-c breaks with increasing temperature, a key features of a good fracturing fluid.

Figure 5:
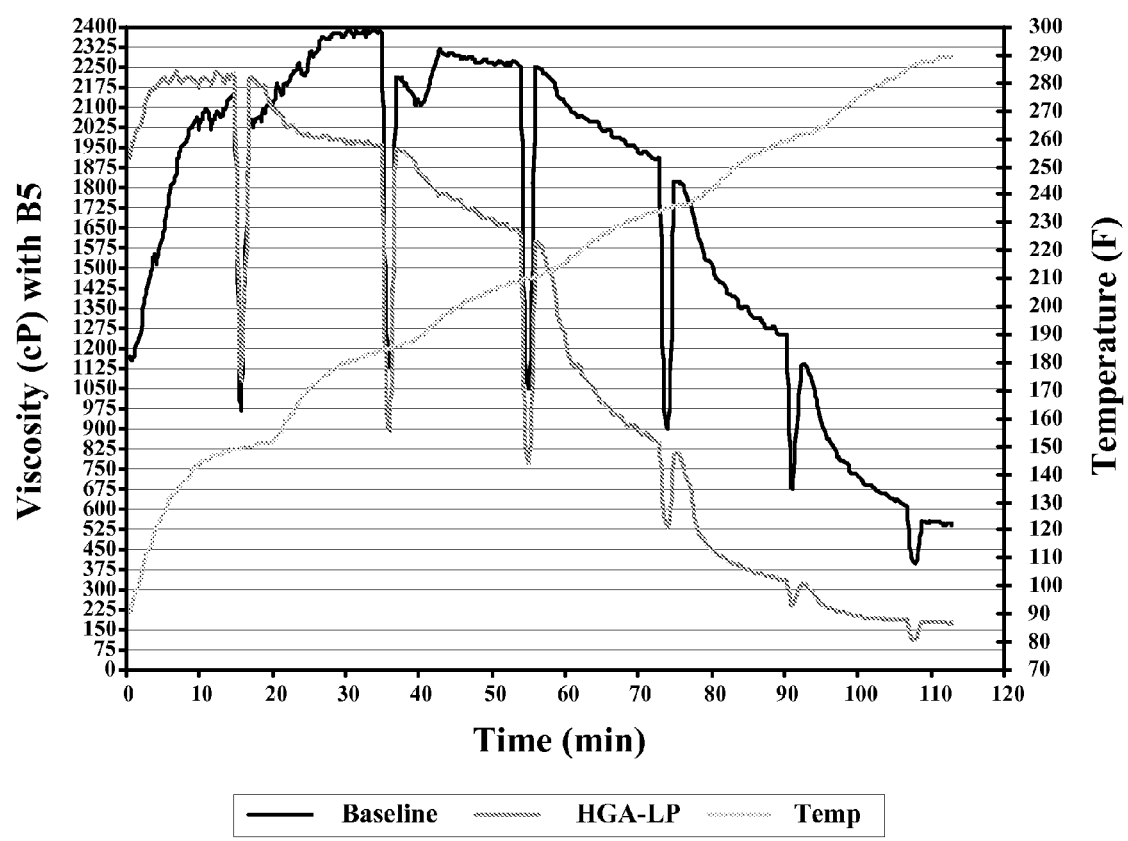
FIG. 5 is a plot depicting the viscosity verses temperature behavior of another fluid embodiment of this invention.

Referring now to FIG. 5, a plot of the viscosity of the composition of Example 9a-c versus temperature shows that the viscosity of the composition of Examples 3a-c breaks with increasing temperature, a key features of a good fracturing fluid.

Figure 6:
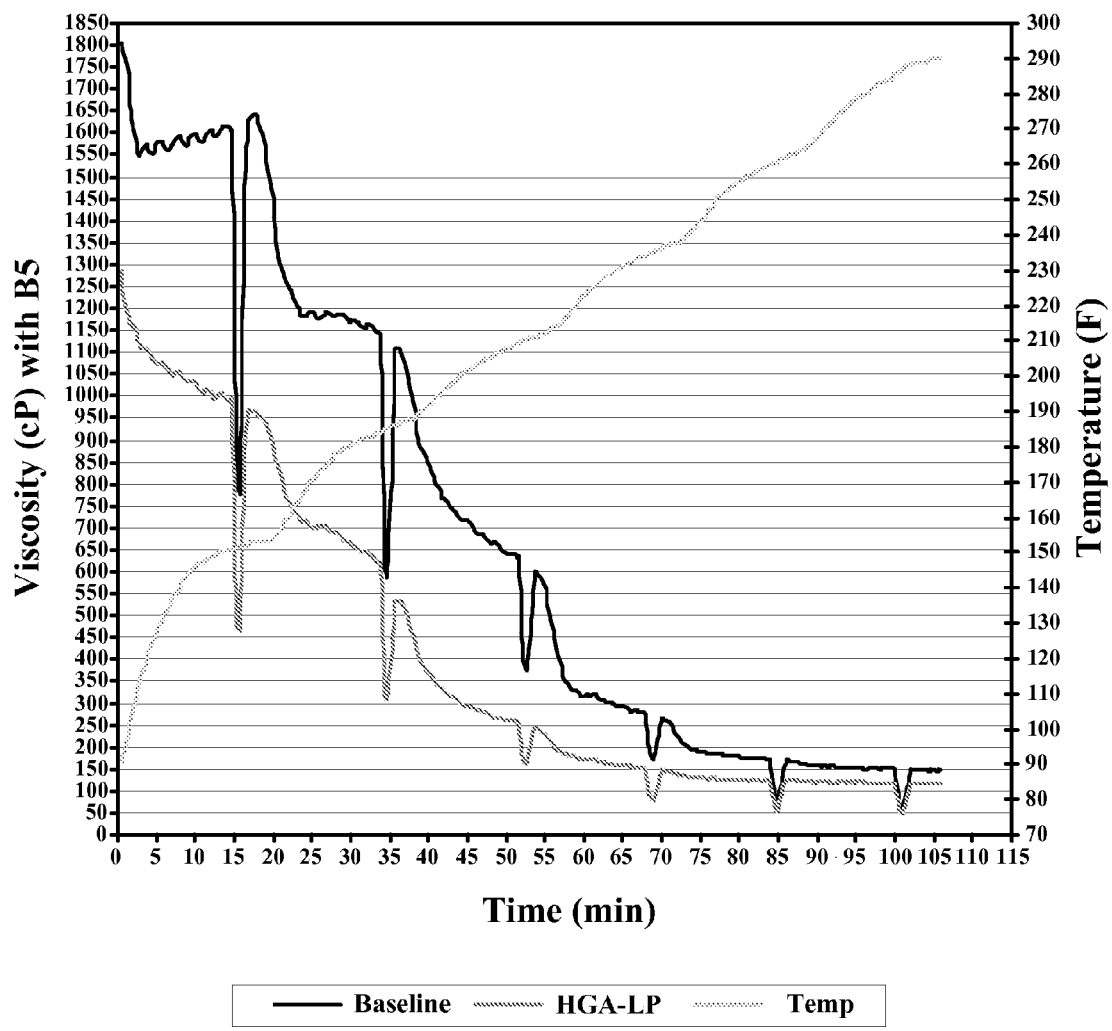
FIG. 6 is a plot depicting the viscosity verses temperature behavior of another fluid embodiment of this invention.

Referring now to FIG. 6, a plot of the viscosity of the composition of Example 10a-c versus temperature shows that the viscosity of the composition of Examples 3a-c breaks with increasing temperature, a key features of a good fracturing fluid.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for making a low volatility phosphate ester composition comprising the step of:
    contacting phosphorus pentoxide with an alkoxide donor under conditions of reaction temperature, reaction pressure and reaction time sufficient to form a phosphate ester product comprising a mixture of $PO(OR)(OH)_2$ and $PO(OR)_2(OH)$ with no or substantially no $PO(OR)_3$, where the product has an acid value at pH 5 to 5.5 between about 190 and about 210, and an acid value at pH 9 to 9.5 between about 230 and about 260, and produces reduced amounts of or no volatile phosphorus-containing compounds at temperatures up to about 250° C., where alkoxide donor comprises a mono-alkyl-phosphate, di-alkyl-phosphate, tri-alkyl-phosphate, or a mixture thereof and an alcohol, where the alkyl groups and the alcohol all have at least 4 carbon atoms and where one or more of carbon atoms can be oxygen and where the reaction temperature is between about 200° F. (93.3° C.) and about 300° F. (148.9° C.) and where the composition is adapted for use in oil and/or gas production and stimulation, while reducing phosphorus-containing deposition on downstream separation equipment.

2. The method of claim 1, wherein the reaction pressure is atmospheric or near atmospheric.

3. The method of claim 1, wherein the period of reaction time is between about 0.5 hours and 12 hours.

4. The method of claim 1, wherein the alkyl groups and/or the alcohol all have between 4 and 20 carbon atoms.

5. The method of claim 1, wherein the alkyl groups and/or the alcohol all have between 4 and 16 carbon atoms.

6. The method of claim 1, wherein the alkyl groups and/or the alcohol all have between 4 and 12 carbon atoms.

7. The method of claim 1, wherein the alkyl groups and/or the alcohol all have between 6 and 12 carbon atoms.

8. The method of claim 1, wherein the alkyl groups and/or the alcohols all have between 8 and 12 carbon atoms.

9. The method of claim 1, wherein the alkyl groups and/or the alcohols all have between 8 and 10 carbon atoms.

10. The composition of claim 1, wherein the product has an acid value at pH 5 to 5.5 is between about 195 and about 205 and acid value at pH 9 to 9.5 of between about 235 and about 255.

11. A method for making upstream oilfield processing fluids having reduced volatile phosphorus values, the fluids comprising:
a base fluid; and
a cross-linkable composition including:
a gelling agent; and
a cross-linking agent,
where the base fluid is a hydrocarbon, the gelling agent comprises a phosphate ester product comprising a mixture of $PO(OR)(OH)_2$ and $PO(OR)_2(OH)$ with no or substantially no $PO(OR)_3$, where the product has an acid value at pH 5 to 5.5 between about 190 and about 210, and an acid value at pH 9 to 9.5 between about 230 and about 260, where the product is formed by contacting phosphorus pentoxide and an alkoxide donor comprises a mono-alkyl-phosphate, di-alkyl-phosphate, tri-alkyl-phosphate, or a mixture thereof and an alcohol, where the alkyl groups and the alcohol all have at least 4 carbon atoms, where one or more of carbon atoms can be oxygen at a reaction temperature between about 200° F. (93.3° C.) and about 300° F. (148.9° C.), and where the fluid produces reduced amounts of or no volatile phosphorus-containing compounds at temperatures up to 250° C. and where the fluids are adapted for use in oil and/or gas production and stimulation, while reducing phosphorus-containing deposition on downstream separation equipment.

12. The method of claim 11, wherein the hydrocarbon base fluid is selected from the group consisting of synthetic hydrocarbon fluids, petroleum based hydrocarbon fluids, natural hydrocarbon fluids and mixtures or combinations thereof.

13. The method of claim 11, wherein the hydrocarbon base fluid is a petroleum based hydrocarbon fluid.

14. The method of claim 11, wherein the hydrocarbon base fluid have viscosities ranging from about $0.5 \times 10^{-6}$ to about $600 \times 10^{-6}$ m²/s (0.5 to about 600 centistokes).

15. The method of claim 11, wherein the alkyl groups and/or the alcohols all have between 4 and 20 carbon atoms.

16. The method of claim 11, wherein the alkyl groups and/or the alcohols all have between 4 and 16 carbon atoms.

17. The method of claim 11, wherein the alkyl groups and/or the alcohols all have between 4 and 12 carbon atoms.

18. The method of claim 11, wherein the alkyl groups and/or the alcohols all have between 6 and 12 carbon atoms.

19. The method of claim 11, wherein the alkyl groups and/or the alcohols all have between 8 and 12 carbon atoms.

20. The method of claim 11, wherein the alkyl groups and/or the alcohols all have between 8 and 10 carbon atoms.

21. The composition of claim 11, wherein the product has an acid value at pH 5 to 5.5 is between about 195 and about 205 and acid value at pH 9 to 9.5 of between about 235 and about 255.

22. A composition comprising a phosphate ester product comprising a mixture of $PO(OR)(OH)_2$ and $PO(OR)_2(OH)$ with no or substantially no $PO(OR)_3$, where the product has an acid value at pH 5 to 5.5 between about 190 and about 210, and an acid value at pH 9 to 9.5 between about 230 and about 260, where the product is formed from contacting phosphorus pentoxide and an alkoxide donor comprises a mono-alkyl-phosphate, di-alkyl-phosphate, tri-alkyl-phosphate, or a mixture thereof and an alcohol, where the alkyl groups and the alcohol all have at least 4 carbon atoms and where one or more of carbon atoms can be oxygen at a temperature between about 200° F. and about 300° F., and where the composition has reduced or no volatility of phosphorus-containing compounds at temperatures up to 250° C. and where the composition is adapted for use in oil and/or gas production, while reducing phosphorus-containing deposition on downstream separation equipment.

23. The composition of claim 22, wherein the alkyl groups and the alcohols all have between 4 and 20 carbon atoms.

24. The composition of claim 22, wherein the alkyl groups and/or the alcohols all have between 4 and 16 carbon atoms.

25. The composition of claim 22, wherein the alkyl groups and/or the alcohols all have between 4 and 12 carbon atoms.

26. The composition of claim 22, wherein the alkyl groups and/or the alcohols all have between 6 and 12 carbon atoms.

27. The composition of claim 22, wherein the alkyl groups and/or the alcohols all have between 8 and 12 carbon atoms.

28. The composition of claim 22, wherein the alkyl groups and/or the alcohols all have between 8 and 10 carbon atoms.

29. The composition of claim 22, wherein the product has an acid value at pH 5 to 5.5 is between about 195 and about 205 and acid value at pH 9 to 9.5 of between about 235 and about 255.

* * * * *